United States Patent
Hell et al.

(10) Patent No.: US 7,417,170 B2
(45) Date of Patent: Aug. 26, 2008

(54) PROCESS FOR THE PREPARATION OF SUBSTITUTED 3-ARYL-BUTYLAMINE COMPOUNDS

(75) Inventors: Wolfgang Hell, Aachen (DE); Markus Kegel, Aachen (DE); Bernhard Akteries, Aachen (DE); Helmut Buschmann, Esplugues de Llobregat (ES); Jorg Holenz, Barcelona (ES); Harmut Loebermann, Aachen (DE); Detlef Heller, Rostock (DE); Hans-Joachim Drexler, Rostock (DE); Stefan Gladow, Buchs (CH)

(73) Assignee: Gruenenthal GmbH, Aachen (DE)

( * ) Notice: Subject to any disclaimer, the term of this patent is extended or adjusted under 35 U.S.C. 154(b) by 112 days.

(21) Appl. No.: 11/294,449

(22) Filed: Dec. 6, 2005

(65) Prior Publication Data

US 2006/0194988 A1    Aug. 31, 2006

Related U.S. Application Data

(63) Continuation of application No. PCT/EP2004/006027, filed on Jun. 4, 2004.

(30) Foreign Application Priority Data

Jun. 6, 2003 (DE) .................. 103 26 097

(51) Int. Cl.
*C07C 209/70* (2006.01)
(52) U.S. Cl. ..................... 564/358; 564/375
(58) Field of Classification Search .............. None
See application file for complete search history.

(56) References Cited

U.S. PATENT DOCUMENTS 5,811,582 A    9/1998    Buschmann et al.
6,248,737 B1   6/2001    Buschmann et al.

FOREIGN PATENT DOCUMENTS

DE    4426245 A1    7/1994
EP    0693475 A1    7/1995
EP    0799819 A1    2/1997

*Primary Examiner*—Brian J Davis
(74) *Attorney, Agent, or Firm*—Crowell & Moring LLP

(57) ABSTRACT

Methods for the dehydration of substituted 1-amino-3-aryl-butan-3-ol compounds for the preparation of substituted 3-aryl-butyl-amine compounds.

58 Claims, No Drawings

PROCESS FOR THE PREPARATION OF SUBSTITUTED 3-ARYL-BUTYLAMINE COMPOUNDS

CROSS REFERENCE TO RELATED APPLICATIONS

This application is a continuation of International Patent Application No. PCT/EP2004/006027, filed Jun. 4, 2004, designating the United States of America, and published in German as WO 2004/108658, the entire disclosure of which is incorporated herein by reference. Priority is claims based on the following Federal Republic of German Patent Application No. DE 103 26 097.8, filed Jun. 6, 2003.

FIELD OF THE INVENTION

The present invention relates to a process for the dehydration of substituted 1-amino-3-aryl-butan-3-ol compounds for the preparation of substituted 3-aryl-butyl-amine compounds.

BACKGROUND OF THE INVENTION

The treatment of chronic and non-chronic states of pain is of great importance in medicine. This is reflected in the large number of publications.

EP 0 693 475 discloses an active compound class of 3-aryl-butyl-amine compounds, in particular dimethyl-(3-aryl-butyl)-amine compounds, with an excellent analgesic activity and very good tolerability.

The preparation of these pharmaceutical active compounds starts from tertiary alcohols, these first being converted into the corresponding chloride compound, which is then reduced with zinc borohydride, zinc cyanoborohydride or tin cyanoborohydride. This process has the disadvantage that the preparation of the chloride compound takes place using comparatively aggressive chlorinating agents, such as thionyl chloride, and this furthermore also has to be used in a high excess. In addition, there is a considerable risk of fire and health hazard from the hydrogenation reagents. This process moreover does not proceed with a satisfactory yield in all cases.

SUMMARY OF THE INVENTION

One object of the present invention is to provide a process for eliminating the tertiary alcohol function from substituted 4-amino-2-aryl-butan-2-ol compounds, with which the correspondingly substituted 3-aryl-butyl-amine compounds are obtained in good yields under environment-friendly conditions. A further aim of the process is to obtain enantiomer purity in the case of the substituted stereochemically pure compounds employed.

This object is achieved according to the invention by providing the process described below for the dehydration of substituted 1-amino-3-aryl-butan-3-ol compounds of the general formula II given below for the preparation of substituted 3-aryl-butyl-amine compounds of the general formula I given below. The compounds of the general formula I are preferably employed as pharmaceutical active compounds in medicaments and are suitable in particular for combating pain.

The present invention therefore provides a process for the preparation of a substituted 3-aryl-butyl-amine compound of the general formula I

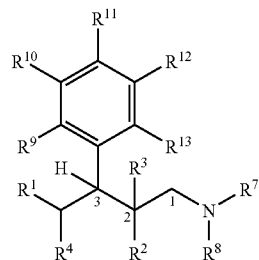

wherein
$R^1$ is chosen from H, $C_{1-3}$-alkyl, branched or unbranched, saturated or unsaturated, unsubstituted or mono- or polysubstituted, $R^2$ and $R^3$ in each case independently of one another are chosen from H or $C_{1-4}$-alkyl, branched or unbranched, saturated or unsaturated, unsubstituted or mono- or polysubstituted, or $R^2$ and $R^3$ together form a saturated $C_{4-7}$-cycloalkyl radical, unsubstituted or mono- or polysubstituted, $R^4$ is chosen from H, $C_{1-3}$-alkyl, branched or unbranched, saturated or unsaturated, unsubstituted or mono- or polysubstituted, $R^7$ and $R^8$ in each case independently of one another are chosen from H or $C_{1-3}$-alkyl, branched or unbranched, saturated or unsaturated, unsubstituted or mono- or polysubstituted, $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; $PO(O-C_{1-4}$-alkyl)$_2$, $CO(OC_{1-5}$-alkyl), $CONH-C_6H_4$-$(C_{1-3}$-alkyl), $CO(C_{1-5}$-alkyl), $CO-CHR^{17}-NHR^{18}$, $CO-C_6H_4-R^{15}$, where $R^{15}$ is ortho-$OCOC_{1-3}$-alkyl or meta- or para-$CH_2N(R^{16})_2$, where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and $R^{18}$ in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, $OCH=CH$, $CH=CHO$, $CH=C(CH_3)O$, $OC(CH_3)=CH$, $(CH_2)_4$ or $OCH=CHO$ ring, in each case in the form of one of its pure stereoisomers, in particular enantiomers or diastereomers, its racemates or in the form of a mixture of stereoisomers, in particular the enantiomers or diastereomers, in any desired mixing ratio, or in each case in the form of a physiologically acceptable salt, or in each case in the form of a solvate, characterized in that in a first step a) a 1-amino-3-aryl-butan-3-ol compound of the general formula II

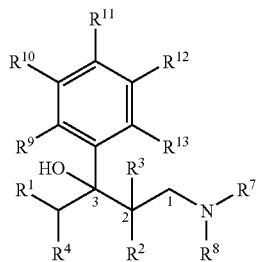

wherein $R^1, R^2, R^3, R^4, R^7, R^8, R^9, R^{10}, R^{11}, R^{12}$ and $R^{13}$ have the abovementioned meaning, in each case optionally in the form of one of its pure stereoisomers, in particular enantiomers or diastereomers, its racemates or in the form of a mixture of stereoisomers, in particular the enantiomers or diastereomers, in any desired mixing ratio, or in each case in the form of a physiologically acceptable salt, or in each case in the form of a solvate, is employed and elimination is carried out under the action of an acid to give a substituted 3-aryl-but-3-enyl-amine compound of the general formula III

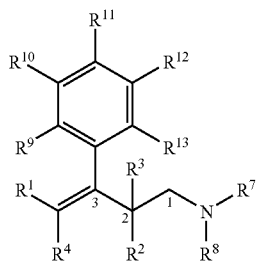

wherein $R^1, R^2, R^3, R^4, R^7, R^8, R^9, R^{10}, R^{11}, R^{12}$ and $R^{13}$ have the abovementioned meaning, in each case optionally in the form of one of its pure stereoisomers, in particular enantiomers or diastereomers, its racemates or in the form of a mixture of stereoisomers, in particular the enantiomers or diastereomers, in any desired mixing ratio, or in each case in the form of a physiologically acceptable salt, or in each case in the form of a solvate, and in a second step b) the substituted 3-aryl-but-3-enyl-amine compound according to the general formula III formed is then hydrogenated under the participation of a metal catalyst and hydrogen to give a substituted 3-aryl-butyl-amine compound of the general formula I.

This process allows a synthesis with high yields, good environment-friendliness and high stereoselectivity.

In the context of this invention, alkyl and cycloalkyl radicals are understood as meaning saturated and unsaturated (but not aromatic), branched, unbranched and cyclic hydrocarbons, which can be unsubstituted or mono- or polysubstituted. Here, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4- or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or $C_{1-8}$-alkyl. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6-, or C7-cycloalkyl, $C_{5-6}$-cycloalkyl represents C5- or C6-cycloalkyl and $C_{5-7}$-cycloalkyl represents C5-, C6- or C7-cycloalkyl. In respect of cycloalkyl, the term also includes saturated cycloalkyls in which one or 2 carbon atoms are replaced by a heteroatom, S, N or O. The term cycloalkyl however also includes, in particular, mono- or poly-, preferably monounsaturated cycloalkyls without a heteroatom in the ring, as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, $CHF_2$, $CF_3$ or $CH_2OH$ as well as pyrazolinone, oxopyrazolinone, [1,4]-dioxane or dioxolane.

In connection with alkyl and cycloalkyl—as long as this is not expressly defined otherwise—the term substituted in the context of this invention is understood here as meaning substitution of at least one (optionally also several) hydrogen radical(s) by F, Cl, Br, I, $NH_2$, SH or OH, "polysubstituted" or "substituted" in the case of multiple substitution being understood as meaning that the substitution occurs several times both on different and on the same atoms by identical or different substituents, for example three times on the same C atom, as in the case of $CF_3$, or at different places, as in the case of —CH(OH)—CH=CH—$CHCl_2$. Particularly preferred substituents here are F, Cl and OH. In respect of cycloalkyl, the hydrogen radical can also be replaced by $OC_{1-3}$-alkyl or $C_{1-3}$-alkyl (in each case mono- or polysubstituted or unsubstituted), in particular methyl, ethyl, n-propyl, i-propyl, $CF_3$, methoxy or ethoxy.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

An aryl radical is understood as meaning ring systems with at least one aromatic ring but without heteroatoms in even only one of the rings. Examples are phenyl, naphthyl, fluoranthenyl, fluorenyl, tetralinyl or indanyl, in particular 9H-fluorenyl or anthracenyl radicals, which can be unsubstituted or mono- or polysubstituted.

A heteroaryl radical is understood as meaning heterocyclic ring systems with at least one unsaturated ring, which contain one or more heteroatoms from the group consisting of nitrogen, oxygen and/or sulfur and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

In connection with aryl and heteroaryl, substituted is understood here as meaning substitution of the aryl or heteroaryl by $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The radical $R^{23}$ here represents H, a $C_{1-10}$-alkyl, preferably a $C_{1-6}$-alkyl, an aryl or heteroaryl or an aryl or heteroaryl radical bonded via a $C_{1-3}$-alkyl group, where these aryl and heteroaryl radicals may not themselves be substituted by aryl or heteroaryl radicals, the radicals $R^{24}$ and $R^{25}$, which are identical or different, represent H, a $C_{1-10}$-alkyl, preferably a $C_{1-6}$-alkyl, an aryl, a heteroaryl or an aryl or heteroaryl radical bonded via a $C_{1-3}$-alkylene group, where these aryl and heteroaryl radicals may not themselves be substituted by aryl or heteroaryl radicals, or the radicals $R^{24}$ and $R^{25}$ together denote $CH_2CH_2OCH_2CH_2$, $CH_2CH_2NR^{26}CH_2CH_2$ or $(CH_2)_{3-6}$, and the radical $R^{26}$ represents H, a $C_{1-10}$-alkyl, preferably a $C_{1-6}$-alkyl, an aryl or heteroaryl radical or an aryl or heteroaryl radical bonded via a $C_{1-3}$-alkylene group, where these aryl and heteroaryl radicals may not themselves be substituted by aryl or heteroaryl radicals.

The term salt in the context of this invention is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes complexed via ionic interactions.

The term of the physiologically acceptable salt (in particular with cations or bases) in the context of this invention is understood as meaning salts of at least one of the compounds according to the invention—usually of a (deprotonated) acid—as the anion with at least one preferably inorganic cation, which are physiologically—especially when used in humans and/or mammals—acceptable. The salts of the alkali metals and alkaline earth metals and also with $NH_4+$ are particularly preferred, but in particular (mono-) or (di-)sodium, (mono-) or (di-)potassium, magnesium or calcium salts.

The term of the physiologically acceptable salt (in particular with anions or acids) in the context of this invention is furthermore understood as meaning salts of at least one of the compounds according to the invention—usually protonated, for example on the nitrogen—as the cation with at least one anion, which are physiologically—especially when used in humans and/or mammals—acceptable. In particular, in the context of this invention this is understood as meaning the salt formed with a physiologically acceptable acid, that is to say salts of the particular active compound with inorganic or organic acids which are physiologically—especially when used in humans and/or mammals—acceptable. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1β6-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid. The hydrochloride salt is particularly preferred.

Suitable salts in the context of this invention and in each use described and each of the medicaments described are salts of the particular active compound with inorganic or organic acids and/or a sugar substitute, such as saccharin, cyclamate or acesulfam. However, the hydrochloride is particularly preferred.

Compounds according to formula I and according to formula II and their preparation are known from DE 44 26 245 A1 and U.S. Pat. No. 6,248,737. Compounds according to formula III are known from EP 799 819 and U.S. Pat. No. 5,811,582.

In some cases it is preferable for the product to be isolated between step a and step b. For this, after the elimination according to step a) the mixture is first neutralized with a base, preferably an ammonium compound or a hydroxide compound, in particular a solution of an alkali metal or alkaline earth metal hydroxide, preferably NaOH or KOH solution, and/or a basic pH, preferably ≧pH 9, in particular ≧pH 10, preferably between pH 10 and pH 12.5, is first established. An organic solvent, preferably a weakly water-soluble, polar organic solvent, in particular an organic acid ester, preferably ethyl acetate or methyl acetate, is then added and the mixture is stirred. This step is also possible without a solvent or using diisopropyl ester. The aqueous phase which remains is then discarded and the desired product is isolated from the organic phase, preferably by distillation, in particular in vacuo.

It is preferable for the process according to the invention if, for compounds according to formula I, formula II and formula III, $R^4$ is chosen from H or $CH_3$, preferably $R^4$ denotes H.

It is preferable for the process according to the invention if, for compounds according to formula I, formula II and formula III, $R^1$ is chosen from $C_{1-3}$-alkyl, saturated or unsaturated, substituted or unsubstituted, branched or unbranched.

It is preferable for the process according to the invention if, for compounds according to formula I, formula II and formula III, $R^4$ is chosen from H or $CH_3$, preferably $R^4$ denotes H, and/or $R^1$ is chosen from $C_{1-3}$-alkyl, saturated or unsaturated, substituted or unsubstituted, branched or unbranched.

It is preferable for the process according to the invention if, for compounds according to formula I, formula II and formula III, $R^7$ and $R^8$ in each case independently of one another are chosen from H or $CH_3$, preferably $R^7$ and $R^8$ denote H or $R^7$ and $R^8$ denote $CH_3$ or $R^7$ denotes H and $R^8$ denotes $CH_3$, in particular $R^7$ and $R^8$ denote $CH_3$.

It is preferable for the process according to the invention if, for compounds according to formula I, formula II and formula III, $R^1$ is chosen from $C_{1-3}$-alkyl, saturated and unsubstituted, branched or unbranched, preferably from $CH_3$, $C_2H_5$, i-propyl or n-propyl, in particular from $CH_3$ or $C_2H_5$.

It is preferable for the process according to the invention if, for compounds according to formula I, formula II and formula III, $R^2$ and $R^3$ independently of one another are chosen from H, $C_{1-4}$-alkyl, saturated and unsubstituted, branched or unbranched; preferably from H, $CH_3$, $C_2H_5$, i-propyl or t-butyl, in particular from H or $CH_3$ or $C_2H_5$.

It is preferable for the process according to the invention if, for compounds according to formula I, formula II and formula III, $R^3$=H and $R^2 \neq$ H,
preferably $R^3$=H and $R^2$=$CH_3$ or $C_2H_5$,
in particular $R^3$=H and $R^2$=$CH_3$.

It is preferable for the process according to the invention if, for compounds according to formula I, formula II and formula III, $R^2$ and $R^3$ together form a $C_{5-6}$-cycloalkyl radical, saturated or unsaturated, unsubstituted or mono- or polysubstituted, preferably saturated and unsubstituted, in particular cyclohexyl.

It is preferable for the process according to the invention if, for compounds according to formula I, formula II and formula III, $R^9$ to $R^{13}$, where 3 or 4 of the radicals $R^9$ to $R^{13}$ must correspond to H, independently of one another are chosen from
H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched;
preferably from H, Cl, F, OH, $CF_2H$, $CF_3$, $OCH_3$ or $SCH_3$ or $R^{12}$ and $R^{11}$ form a 3,4-OCH=CH ring in particular
if $R^9$, $R^{11}$ and $R^{13}$ correspond to H, one of $R^{10}$ or $R^{12}$ also corresponds to H, while the other is chosen from:
Cl, F, OH, $CF_2H$, $CF_3$, $OR^{14}$ or $SR^{14}$, preferably from OH, $CF_2H$, $OCH_3$ or $SCH_3$
or
if $R^9$ and $R^{13}$ correspond to H and $R^{11}$ corresponds to OH, $OCH_3$, Cl or F, preferably Cl, one of $R^{10}$ or $R^{12}$ also corresponds to H, while the other corresponds to OH, $OCH_3$, Cl or F, preferably Cl,
or
if $R^9$, $R^{10}$, $R^{12}$ and $R^{13}$ correspond to H, $R^{11}$ is chosen from $CF_3$, $CF_2H$, Cl or F, preferably from F,
or
if $R^{10}$, $R^{11}$ and $R^{12}$ correspond to H, one of $R^9$ or $R^{13}$ also corresponds to H, while the other is chosen from OH, $OC_2H_5$ or $OC_3H_7$.

It is preferable for the process according to the invention if, for compounds according to formula I, formula II and formula III, $R^1$ is chosen from
$C_{1-3}$-alkyl, saturated and unsubstituted, branched or unbranched; preferably $CH_3$, $C_2H_5$, or $C_3H_7$, in particular $CH_3$ or $C_2H_5$, and/or
$R^2$ and $R^3$ independently of one another are chosen from
H, $C_{1-4}$-alkyl, saturated and unsubstituted, branched or unbranched; preferably from H, $CH_3$, $C_2H_5$, i-propyl or t-butyl, in particular from H or $CH_3$ or $C_2H_5$,
preferably:
$R^3$=H and $R^2 \neq$ H,
preferably $R^3$=H and $R^2$=$CH_3$ or $C_2H_5$,
in particular $R^3$=H and $R^2$=$CH_3$,
or
$R^2$ and $R^3$ together form a $C_{5-6}$-cycloalkyl radical, saturated or unsaturated, unsubstituted or mono- or polysubstituted, preferably saturated and unsubstituted, in particular cyclohexyl, and/or
$R^4$ is chosen from H, and/or
$R^7$ and $R^8$ in each case independently of one another are chosen from
H or $CH_3$,
preferably $R^7$ and $R^8$ denote H or $R^7$ and $R^8$ denote $CH_3$ or $R^7$ denotes H and $R^8$ denotes $CH_3$,
in particular $R^7$ and $R^8$ denote $CH_3$;

and/or
$R^9$ to $R^{13}$, where 3 or 4 of the radicals $R^9$ to $R^{13}$ must correspond to H, independently of one another are chosen from
H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched;
preferably from H, Cl, F, OH, $CF_2H$, $CF_3$, $OCH_3$ or $SCH_3$ or $R^{12}$ and $R^{11}$ form a 3,4-OCH=CH ring in particular
if $R^9$, $R^{11}$ and $R^{13}$ correspond to H, one of $R^{10}$ or $R^{12}$ also corresponds to H, while the other is chosen from:
Cl, F, OH, $CF_2H$, $CF_3$, $OR^{14}$ or $SR^{14}$, preferably from OH, $CF_2H$, $OCH_3$ or $SCH_3$
or
if $R^9$ and $R^{13}$ correspond to H and $R^{11}$ corresponds to OH, $OCH_3$, Cl or F, preferably Cl, one of $R^{10}$ or $R^{12}$ also corresponds to H, while the other corresponds to OH, $OCH_3$, Cl or F, preferably Cl,
or
if $R^9$, $R^{10}$, $R^{12}$ and $R^{13}$ correspond to H, $R^{11}$ is chosen from $CF_3$, $CF_2H$, Cl or F, preferably from F,
or
if $R^{10}$, $R^{11}$ and $R^{12}$ correspond to H, one of $R^9$ or $R^{13}$ also corresponds to H, while the other is chosen from OH, $OC_2H_5$ or $OC_3H_7$.

It is preferable for the process according to the invention if, for compounds according to formula I where $R^3$=H and $R^2 \neq$ H, these are in the configurations Ia or Ib

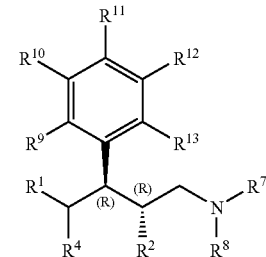

Ia

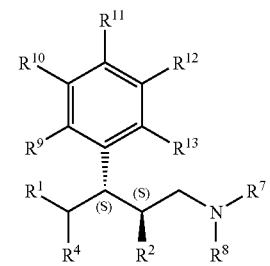

Ib

It is preferable for the process according to the invention if, for compounds according to formula II where $R^3$=H and $R^2 \neq$ H, these are in the configurations IIa or IIb

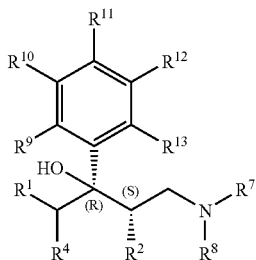

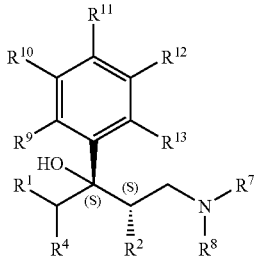

or in the configurations IIc and IId

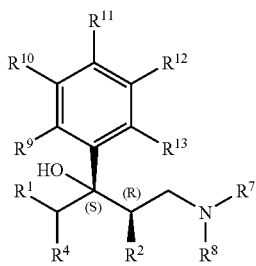

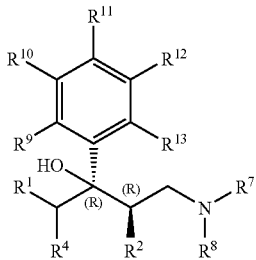

It is preferable for the process according to the invention if, for compounds according to formula III where $R^3$=H, $R^2 \neq$H, $R^4$=H and $R^1 \neq$H, these are in the configurations IIIa or IIIb

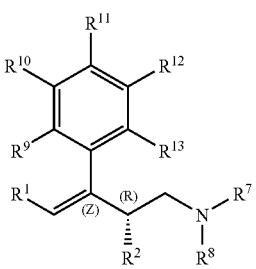

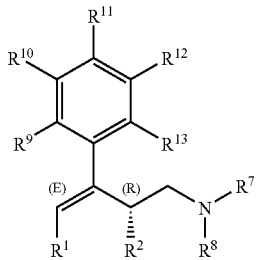

or for compounds according to formula III where $R^3$=H, $R^2 \neq$H, $R^4$=H and $R^1 \neq$H, these are in the configurations IIIc or IIId

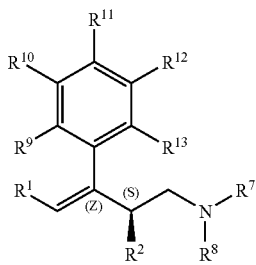

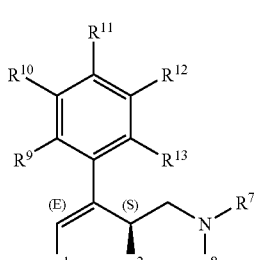

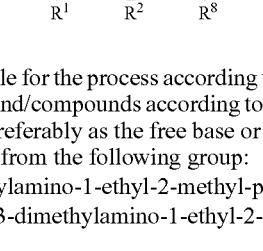

It is preferable for the process according to the invention if, for the compound/compounds according to formula I, at least one of these, preferably as the free base or as the hydrochloride, is chosen from the following group:

3-(3-dimethylamino-1-ethyl-2-methyl-propyl)-phenol,
(1R,2R)-3-(3-dimethylamino-1-ethyl-2-methyl-propyl)-phenol
(−)-(1R,2R)-3-(3-dimethylamino-1-ethyl-2-methyl-propyl)-phenol,
(1S,2S)-3-(3-dimethylamino-1-ethyl-2-methyl-propyl)-phenol
(+)-(1S,2S)-3-(3-dimethylamino-1-ethyl-2-methyl-propyl)-phenol
(±)-(1RS,2RS)-3-(3-dimethylamino-1-ethyl-2-methyl-propyl)-phenol
rac-(1RS,2RS)-3-(3-dimethylamino-1-ethyl-2-methyl-propyl)-phenol,
[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine, (+)-(2S,3S)-[3-(3-methoxy-phenyl)-2-methyl-pentyl]-dimethylamine,
(±)-(2RS,3RS)-[3-(3-methoxy-phenyl)-2-methyl-pentyl]-dimethylamine,
rac(2RS,3RS)-[3-(3-methoxy-phenyl)-2-methyl-pentyl]-dimethylamine,
3{[3-(p-isopropyl-phenyl-carbamoyl)-oxy-phenyl]-2-methyl-pentyl}-dimethylamine,
(2R,3R)-{3 [3-(p-isopropyl-phenyl-carbamoyl)-oxy-phenyl]-2-methyl-pentyl}-dimethylamine,
(2S,3S)-{3 [3-(p-isopropyl-phenyl-carbamoyl)-oxy-phenyl]-2-methyl-pentyl}-dimethylamine,
(2SR,3SR)-{3 [3-(p-isopropyl-phenyl-carbamoyl)-oxy-phenyl]-2-methyl-pentyl}-dimethylamine preferably
3-(3-dimethylamino-1-ethyl-2-methyl-propyl)-phenol,
(1R,2R)-3-(3-dimethylamino-1-ethyl-2-methyl-propyl)-phenol,
(−)-(1R,2R)-3-(3-dimethylamino-1-ethyl-2-methyl-propyl)-phenol,
(1S,2S)-3-(3-dimethylamino-1-ethyl-2-methyl-propyl)-phenol,
(+)-(1S,2S)-3-(3-dimethylamino-1-ethyl-2-methyl-propyl)-phenol,
(±)-(1RS,2RS)-3-(3-dimethylamino-1-ethyl-2-methyl-propyl)-phenol,
rac-(1RS,2RS)-3-(3-dimethylamino-1-ethyl-2-methyl-propyl)-phenol,
[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine,
(+)-(2S,3S)-[3-(3-methoxy-phenyl)-2-methyl-pentyl]-dimethylamine, in particular
[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine,
(+)-(2S,3S)-[3-(3-methoxy-phenyl)-2-methyl-pentyl]-dimethylamine.

It is preferable for the process according to the invention if, for the compound/compounds according to formula II employed, at least one of these, preferably as the free base or as the hydrochloride, is chosen from the following group:
3-(3-dimethylamino-1-ethyl-1-hydroxy-2-methyl-propyl)-phenol,
(1S,2S)-3-(3-dimethylamino-1-ethyl-1-hydroxy-2-methyl-propyl)-phenol,
(1R,2S)-3-(3-dimethylamino-1-ethyl-1-hydroxy-2-methyl-propyl)-phenol,
(1RS,2SS)-3-(3-dimethylamino-1-ethyl-1-hydroxy-2-methyl-propyl)-phenol,
(1S,2R)-3-(3-dimethylamino-1-ethyl-1-hydroxy-2-methyl-propyl)-phenol,
(1R,2R)-3-(3-dimethylamino-1-ethyl-1-hydroxy-2-methyl-propyl)-phenol,
(1RS,2RR)-3-(3-dimethylamino-1-ethyl-1-hydroxy-2-methyl-propyl)-phenol,
[3-(3-methoxy-phenyl)-2-methyl-pentan-3-ol]-dimethylamine,
(2S,3S)-[3-(3-methoxy-phenyl)-2-methyl-pentan-3-ol]-dimethylamine,
(2S,3R)-[3-(3-methoxy-phenyl)-2-methyl-pentan-3-ol]-dimethylamine,
(2SS,3RS)-[3-(3-methoxy-phenyl)-2-methyl-pentan-3-ol]-dimethylamine,
(2R,3S)-[3-(3-methoxy-phenyl)-2-methyl-pentan-3-ol]-dimethylamine,
(2R,3R)-[3-(3-methoxy-phenyl)-2-methyl-pentan-3-ol]-dimethylamine
(2RR,3RS)-[3-(3-methoxy-phenyl)-2-methyl-pentan-3-ol]-dimethylamine,
{3 [3-(p-isopropyl-phenyl-carbamoyl)-oxy-phenyl]-2-methyl-pentan-3-ol}-dimethylamine,
(2S,3R)-{3 [3-(p-isopropyl-phenyl-carbamoyl)-oxy-phenyl]-2-methyl-pentan-3-ol}-dimethylamine,
(2S,3S)-{3 [3-(p-isopropyl-phenyl-carbamoyl)-oxy-phenyl]-2-methyl-pentan-3-ol}-dimethylamine
(2SS,3RS)-{3 [3-(p-isopropyl-phenyl-carbamoyl)-oxy-phenyl]-2-methyl-pentan-3-ol}-dimethylamine,
(2R,3S)-{3 [3-(p-isopropyl-phenyl-carbamoyl)-oxy-phenyl]-2-methyl-pentan-3-ol}-dimethylamine,
(2R,3R)-{3 [3-(p-isopropyl-phenyl-carbamoyl)-oxy-phenyl]-2-methyl-pentan-3-ol}-dimethylamine,
(2RR,3RS)-{3 [3-(p-isopropyl-phenyl-carbamoyl)-oxy-phenyl]-2-methyl-pentan-3-ol}-dimethylamine, preferably
3-(3-dimethylamino-1-ethyl-1-hydroxy-2-methyl-propyl)-phenol,
(1S,2S)-3-(3-dimethylamino-1-ethyl-1-hydroxy-2-methyl-propyl)-phenol,
(1R,2S)-3-(3-dimethylamino-1-ethyl-1-hydroxy-2-methyl-propyl)-phenol,
(1RS,2SS)-3-(3-dimethylamino-1-ethyl-1-hydroxy-2-methyl-propyl)-phenol,
(1S,2R)-3-(3-dimethylamino-1-ethyl-1-hydroxy-2-methyl-propyl)-phenol,
(1R,2R)-3-(3-dimethylamino-1-ethyl-1-hydroxy-2-methyl-propyl)-phenol,
(1RS,2RR)-3-(3-dimethylamino-1-ethyl-1-hydroxy-2-methyl-propyl)-phenol,
[3-(3-methoxy-phenyl)-2-methyl-pentan-3-ol]-dimethylamine,
(2S,3S)-[3-(3-methoxy-phenyl)-2-methyl-pentan-3-ol]-dimethylamine,
(2S,3R)-[3-(3-methoxy-phenyl)-2-methyl-pentan-3-ol]-dimethylamine,
(2SS,3RS)-[3-(3-methoxy-phenyl)-2-methyl-pentan-3-ol]-dimethylamine,
(2R,3S)-[3-(3-methoxy-phenyl)-2-methyl-pentan-3-ol]-dimethylamine,
(2R,3R)-[3-(3-methoxy-phenyl)-2-methyl-pentan-3-ol]-dimethylamine,
(2RR,3RS)-[3-(3-methoxy-phenyl)-2-methyl-pentan-3-ol]-dimethylamine, in particular
[3-(3-methoxy-phenyl)-2-methyl-pentan-3-ol]-dimethylamine,
(2S,3S)-[3-(3-methoxy-phenyl)-2-methyl-pentan-3-ol]-dimethylamine,
(2S,3R)-[3-(3-methoxy-phenyl)-2-methyl-pentan-3-ol]-dimethylamine,
(2SS,3RS)-[3-(3-methoxy-phenyl)-2-methyl-pentan-3-ol]-dimethylamine, (2R,3S)-[3-(3-methoxy-phenyl)-2-methyl-pentan-3-ol]-dimethylamine,
(2R,3R)-[3-(3-methoxy-phenyl)-2-methyl-pentan-3-ol]-dimethylamine,
(2RR,3RS)-[3-(3-methoxy-phenyl)-2-methyl-pentan-3-ol]-dimethylamine, preferably
(2S,3S)-[3-(3-methoxy-phenyl)-2-methyl-pentan-3-ol]-dimethylamine,
(2S,3R)-[3-(3-methoxy-phenyl)-2-methyl-pentan-3-ol]-dimethylamine, or
(2R,3R)-[3-(3-methoxy-phenyl)-2-methyl-pentan-3-ol]-dimethylamine or
(2R,3S)-[3-(3-methoxy-phenyl)-2-methyl-pentan-3-ol]-dimethylamine.

It is preferable for the process according to the invention if, for the compound/compounds according to formula III, at least one of these, preferably as the free base or as the hydrochloride, is chosen from the following group
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl)-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol,
(Z,E)-(2S)-3-(3-dimethylamino-1-ethenyl-2-methyl-propyl)-phenol,
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol,
(Z,E)-(2S)-3-(3-dimethylamino-1-ethenyl-2-methyl-propyl)-phenol,
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine,
{3 [3-(p-isopropyl-phenyl-carbamoyl)-oxy-phenyl]-2-methyl-pent-3-enyl}-dimethylamine,
(Z)-(2R)-{3 [3-(p-isopropyl-phenyl-carbamoyl)-oxy-phenyl]-2-methyl-pent-3-enyl}-dimethylamine,
(E)-(2R)-{3 [3-(p-isopropyl-phenyl-carbamoyl)-oxy-phenyl]-2-methyl-pent-3-enyl}-dimethylamine,
(Z,E)-(2R)-{3 [3-(p-isopropyl-phenyl-carbamoyl)-oxy-phenyl]-2-methyl-pent-3-enyl}-dimethylamine,
(Z)-(2S)-{3 [3-(p-isopropyl-phenyl-carbamoyl)-oxy-phenyl]-2-methyl-pent-3-enyl}-dimethylamine,
(E)-(2S)-{3 [3-(p-isopropyl-phenyl-carbamoyl)-oxy-phenyl]-2-methyl-pent-3-enyl}-dimethylamine,
(Z,E)-(2S)-{3 [3-(p-isopropyl-phenyl-carbamoyl)-oxy-phenyl]-2-methyl-pent-3-enyl}-dimethylamine, preferably
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl)-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol,
(Z,E)-(2S)-3-(3-dimethylamino-1-ethenyl-2-methyl-propyl)-phenol,
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine, in particular
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine, preferably
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine or
(Z,E)-(2R)-[3-(3-methoxy-phenyl)-2-methyl-pent-3-enyl]-dimethylamine, or
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine or
(Z,E)-(2S)-[3-(3-methoxy-phenyl)-2-methyl-pent-3-enyl]-dimethylamine.

It is particularly preferable for the process according to the invention if a chiral center is present in the compound according to formula II employed, at position 2 according to formula II.

It is particularly preferable for the process according to the invention if a chiral center is present in the compound according to formula I, at position 2 according to formula I.

It is preferable for the process according to the invention if a chiral center is present in the compound according to formula III, at position 2 according to formula III.

It is preferable for the process according to the invention if the compound according to formula II employed is enantiomerically pure.

It is preferable for the process according to the invention if the compound according to formula II employed is diastereomerically pure.

It is preferable for the process according to the invention if the compound according to formula II employed is enantiomerically and diastereomerically pure.

It is particularly preferable for the process according to the invention if the compound according to formula II employed is chosen from:
  (2S),3S)-[3-(3-methoxy-phenyl)-2-methyl-pentan-3-ol]-dimethylamine,
  (2S,3R)-[3-(3-methoxy-phenyl)-2-methyl-pentan-3-ol]-dimethylamine or is a mixture of (2S,3S)-[3-(3-methoxy-phenyl)-2-methyl-pentan-3-ol]-dimethylamine and (2S,3R)-[3-(3-methoxy-phenyl)-2-methyl-pentan-3-ol]-dimethylamine, or (2SS,3RS)-[3-(3-methoxy-phenyl)-2-methyl-pentan-3-ol]-dimethylamine.

It is particularly preferable for the process according to the invention if the compound according to formula II employed is chosen from:
  (2R,3R)-[3-(3-methoxy-phenyl)-2-methyl-pentan-3-ol]-dimethylamine,
  (2R,3S)-[3-(3-methoxy-phenyl)-2-methyl-pentan-3-ol]-dimethylamine or is a mixture of (2R,3R)-[3-(3-methoxy-phenyl)-2-methyl-pentan-3-ol]-dimethylamine and (2R,3S)-[3-(3-methoxy-phenyl)-2-methyl-pentan-3-ol]-dimethylamine, or (2RR,3RS)-[3-(3-methoxy-phenyl)-2-methyl-pentan-3-ol]-dimethylamine.

It is preferable for the process according to the invention if the compound according to formula II employed is chosen from:
  (2S,3S)-1-dimethylamino-3-(3-methoxy-phenyl)-2-methyl-pentan-3-ol,
  (2S,3R)-1-dimethylamino-3-(3-methoxy-phenyl)-2-methyl-pentan-3-ol or is a mixture of (2S,3S)-1-dimethylamino-3-(3-methoxy-phenyl)-2-methyl-pentan-3-ol and (2S,3R)-1-dimethylamino-3-(3-methoxy-phenyl)-2-methyl-pentan-3-ol, or (2SS,3RS)-[3-(3-methoxy-phenyl)-2-methyl-pentan-3-ol]-dimethylamine.

It is preferable for the process according to the invention if the compound according to formula II employed is chosen from:
  (2R,3R)-1-dimethylamino-3-(3-methoxy-phenyl)-2-methyl-pentan-3-ol,
  (2R,3S)-1-dimethylamino-3-(3-methoxy-phenyl)-2-methyl-pentan-3-ol or is a mixture of (2R,3R)-1-dimethylamino-3-(3-methoxy-phenyl)-2-methyl-pentan-3-ol and (2R,3S)-1-dimethylamino-3-(3-methoxy-phenyl)-2-methyl-pentan-3-ol, or (2RR,3RS)-[3-(3-methoxy-phenyl)-2-methyl-pentan-3-ol]-dimethylamine.

It is preferable for the process according to the invention if organic acids or halogen halide acids are used in step a).

It is preferable for the process according to the invention if formic acid, hydrochloric acid or hydrobromic acid are used in step a).

It is preferable for the process according to the invention if formic acid is used in step a).

It is preferable for the process according to the invention if hydrochloric acid is used in step a).

It is preferable for the process according to the invention if hydrobromic acid is used in step a).

It is preferable for the process according to the invention if the acid in step a) is employed in a high concentration.

It is preferable for the process according to the invention if the hydrochloric acid in step a) is >20%, preferably >30%, in particular >35%.

It is preferable for the process according to the invention if, after step a), the compounds according to formula III which have undergone elimination are crystallized with hydrochloric acid gas.

It is preferable for the process according to the invention if the reaction time of step a) is between 2 and 10 h, preferably between 3 and 8 h, in particular between 4 and 6 h.

It is preferable for the process according to the invention if the reaction temperature in step a) is between 35 and 100° C., preferably 45 and 80° C., in particular between 50 and 60° C.

It is preferable for the process according to the invention if the solvent in step a) is chosen from:
  $H_2O$ or alcohol or aqueous alcohol solutions.

It is preferable for the process according to the invention if the solvent in step a) is aqueous acid.

It is preferable for the process according to the invention if, in step a), the compound according to formula II employed is dissolved in aqueous acid.

It is preferable for the process according to the invention if, in step a), the compound according to formula II employed is dissolved in aqueous hydrochloric acid.

It is preferable for the process according to the invention if, in step b), the solvent is chosen from:
  $H_2O$ or alcohol or aqueous alcoholic or aqueous acidic solutions, preferably from aqueous acidic solutions.

It is preferable for the process according to the invention if, in step b), the solvent is chosen from:
  $H_2O$ or ethanol or aqueous ethanolic solution or aqueous hydrochloric acid, preferably from aqueous hydrochloric acid.

It is preferable for the process according to the invention if, in step b), the catalyst used comprises a noble metal, preferably platinum, gold or palladium, in particular palladium.

It is preferable for the process according to the invention if, in step b), the catalyst used is palladium-on-active charcoal or palladium(II) chloride.

It is preferable for the process according to the invention if, in step b), the catalyst used is palladium-on-active charcoal (1-10 wt. %, preferably 5 wt. %).

It is preferable for the process according to the invention if the temperature in step b) is kept between 20 and 40° C., preferably between 20 and 35, in particular 25° C.

It is preferable for the process according to the invention if, in step b), an inert gas atmosphere, in particular a nitrogen inert gas, is applied before the hydrogenation.

It is preferable for the process according to the invention if, in step b), the hydrogenation step takes place under a hydrogen pre-pressure of 3-10 bar, preferably 4-7 bar, in particular 5 bar and/or the hydrogenation step takes place under a hydrogen internal pressure of 0.5-3 bar, preferably 0.75-2 bar, in particular 1 bar.

It is preferable for the process according to the invention if, in step b), the starting substances are highly dilute/diluted in the solvent at the start.

It is preferable for the process according to the invention if the solvent for both steps a) and b) is an aqueous acidic solution, preferably aqueous hydrochloric acid.

It is preferable for the process according to the invention if no product is isolated between step a) and step b). It is particularly preferable here if the starting substances are highly dilute/diluted in the solvent at the start or the compound according to formula II employed is dissolved in aqueous acid, in particular the compound according to formula II employed is dissolved in aqueous hydrochloric acid.

The invention also provides a process, called part process in the following, for the preparation of a substituted 3-aryl-butyl-amine compound of the general formula I

I wherein $R^1$ is chosen from H, $C_{1-3}$-alkyl, branched or unbranched, saturated or unsaturated, unsubstituted or mono- or polysubstituted, $R^2$ and $R^3$ in each case independently of one another are chosen from H or $C_{1-4}$-alkyl, branched or unbranched, saturated or unsaturated, unsubstituted or mono- or polysubstituted, or $R^2$ and $R^3$ together form a saturated $C_{4-7}$-cycloalkyl radical, unsubstituted or mono- or polysubstituted, $R^4$ is chosen from H, $C_{1-3}$-alkyl, branched or unbranched, saturated or unsaturated, unsubstituted or mono- or polysubstituted, $R^7$ and $R^8$ in each case independently of one another are chosen from H or $C_{1-3}$-alkyl, branched or unbranched, saturated or unsaturated, unsubstituted or mono- or polysubstituted, $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; $PO(O-C_{1-4}$-alkyl$)_2$, $CO(OC_{1-5}$-alkyl), $CONH-C_6H_4$-$(C_{1-3}$-alkyl), $CO(C_{1-5}$-alkyl), $CO-CHR^{17}-NHR^{18}$, $CO-C_6H_4-R^{15}$, where $R^{15}$ is ortho-$OCOC_{1-3}$-alkyl or meta- or para-$CH_2N(R^{16})_2$, where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and $R^{18}$ in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, $OCH=CH$, $CH=CHO$, $CH=C(CH_3)O$, $OC(CH_3)=CH$, $(CH_2)_4$ or $OCH=CHO$ ring, in each case in the form of one of its pure stereoisomers, in particular enantiomers or diastereomers, its racemates or in the form of a mixture of stereoisomers, in particular the enantiomers or diastereomers, in any desired mixing ratio, or in each case in the form of a physiologically acceptable salt, or in each case in the form of a solvate, characterized in that a substituted 3-aryl-but-3-enyl-amine compound of the general formula III

III wherein $R^1$, $R^2$, $R^3$, $R^4$, $R^7$, $R^8$, $R^9$, $R^{10}$, $R^{11}$, $R^{12}$ and $R^{13}$ have the abovementioned meaning, in each case optionally in the form of one of its pure stereoisomers, in particular enantiomers or diastereomers, its racemates or in the form of a mixture of stereoisomers, in particular the enantiomers or diastereomers, in any desired mixing ratio, or in each case in the form of a physiologically acceptable salt, or in each case in the form of a solvate, is hydrogenated with the participation of a metal catalyst and hydrogen to give a substituted 3-aryl-butyl-amine compound of the general formula I.

It is particularly preferable for the part process according to the invention if, for compounds according to formula I and formula III, $R^4$ is chosen from H or $CH_3$, preferably $R^4$ denotes H.

It is particularly preferable for the part process according to the invention if, for compounds according to formula I and formula III, $R^1$ is chosen from $C_{1-3}$-alkyl, saturated or unsaturated, substituted or unsubstituted, branched or unbranched.

It is particularly preferable for the part process according to the invention if, for compounds according to formula I and formula III, $R^4$ is chosen from H or $CH_3$, preferably $R^4$ denotes H, and/or $R^1$ is chosen from $C_{1-3}$-alkyl, saturated or unsaturated, substituted or unsubstituted, branched or unbranched.

It is particularly preferable for the part process according to the invention if, for compounds according to formula I and formula III, $R^7$ and $R^8$ in each case independently of one another are chosen from H or $CH_3$, preferably $R^7$ and $R^8$ denote H or $R^7$ and $R^8$ denote $CH_3$ or $R^7$ denotes H and $R^8$ denotes $CH_3$, in particular $R^7$ and $R^8$ denote $CH_3$.

It is particularly preferable for the part process according to the invention if, for compounds according to formula I and formula III, $R^1$ is chosen from $C_{1-3}$-alkyl, saturated and unsubstituted, branched or unbranched, preferably from $CH_3$, $C_2H_5$, i-propyl or n-propyl, in particular from $CH_3$ or $C_2H_5$.

It is particularly preferable for the part process according to the invention if, for compounds according to formula I and formula III, $R^2$ and $R^3$ independently of one another are chosen from H, $C_{1-4}$-alkyl, saturated and unsubstituted, branched or unbranched; preferably from H, $CH_3$, $C_2H_5$, i-propyl or t-butyl, in particular from H or $CH_3$ or $C_2H_5$.

It is particularly preferable for the part process according to the invention if, for compounds according to formula I and formula III, $R^3$=H and $R^2 \neq H$, preferably $R^3$=H and $R^2$=$CH_3$ or $C_2H_5$, in particular $R^3$=H and $R^2$=$CH_3$.

It is particularly preferable for the part process according to the invention if, for compounds according to formula I and formula III, $R^2$ and $R^3$ together form a $C_{5-6}$-cycloalkyl radical, saturated or unsaturated, unsubstituted or mono- or polysubstituted, preferably saturated and unsubstituted, in particular cyclohexyl.

It is particularly preferable for the part process according to the invention if, for compounds according to formula I and formula III, $R^9$ to $R^{13}$, where 3 or 4 of the radicals $R^9$ to $R^{13}$ must correspond to H, independently of one another are chosen from H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched;

preferably from H, Cl, F, OH, $CF_2H$, $CF_3$, $OCH_3$ or $SCH_3$ or $R^{12}$ and $R^{11}$ form a 3,4-OCH=CH ring in particular if $R^9$, $R^{11}$ and $R^{13}$ correspond to H, one of $R^{10}$ or $R^{12}$ also corresponds to H, while the other is chosen from:

Cl, F, OH, $CF_2H$, $CF_3$, $OR^{14}$ or $SR^{14}$, preferably from OH, $CF_2H$, $OCH_3$ or $SCH_3$ or if $R^9$ and $R^{13}$ correspond to H and $R^{11}$ corresponds to OH, $OCH_3$, Cl or F, preferably Cl, one of $R^{10}$ or $R^{12}$ also corresponds to H, while the other corresponds to OH, $OCH_3$, Cl or F, preferably Cl, or if $R^9$, $R^{10}$, $R^{12}$ and $R^{13}$ correspond to H, $R^{11}$ is chosen from $CF_3$, $CF_2H$, Cl or F, preferably from F, or if $R^{10}$, $R^{11}$ and $R^{12}$ correspond to H, one of $R^9$ or $R^{13}$ also corresponds to H, while the other is chosen from OH, $OC_2H_5$ or $OC_3H_7$.

It is particularly preferable for the part process according to the invention if, for compounds according to formula I and formula III, $R^1$ is chosen from $C_{1-3}$-alkyl, saturated and unsubstituted, branched or unbranched; preferably $CH_3$, $C_2H_5$, or $C_3H_7$, in particular $CH_3$ or $C_2H_5$, and/or $R^2$ and $R^3$ independently of one another are chosen from H, $C_{1-4}$-alkyl, saturated and unsubstituted, branched or unbranched; preferably from H, $CH_3$, $C_2H_5$, i-propyl or t-butyl, in particular from H or $CH_3$ or $C_2H_5$, preferably:

$R^3$=H and $R^2 \neq H$, preferably $R^3$=H and $R^2$=$CH_3$ or $C_2H_5$, in particular $R^3$=H and $R^2$=$CH_3$, or $R^2$ and $R^3$ together form a $C_{5-6}$-cycloalkyl radical, saturated or unsaturated, unsubstituted or mono- or polysubstituted, preferably saturated and unsubstituted, in particular cyclohexyl, and/or $R^4$ is chosen from H, and/or $R^7$ and $R^8$ in each case independently of one another are chosen from H or $CH_3$, preferably $R^7$ and $R^8$ denote H or $R^7$ and $R^8$ denote $CH_3$ or $R^7$ denotes H and $R^8$ denotes $CH_3$, in particular $R^7$ and $R^8$ denote $CH_3$;

and/or $R^9$ to $R^{13}$, where 3 or 4 of the radicals $R^9$ to $R^{13}$ must correspond to H, independently of one another are chosen from H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched;

preferably from H, Cl, F, OH, $CF_2H$, $CF_3$, $OCH_3$ or $SCH_3$ or $R^{12}$ and $R^{11}$ form a 3,4-OCH=CH ring in particular if $R^9$, $R^{11}$ and $R^{13}$ correspond to H, one of $R^{10}$ or $R^{12}$ also corresponds to H, while the other is chosen from:

Cl, F, OH, $CF_2H$, $CF_3$, $OR^{14}$ or $SR^{14}$, preferably from OH, $CF_2H$, $OCH_3$ or $SCH_3$ or if $R^9$ and $R^{13}$ correspond to H and $R^{11}$ corresponds to OH, $OCH_3$, Cl or F, preferably Cl, one of $R^{10}$ or $R^{12}$ also corresponds to H, while the other corresponds to OH, $OCH_3$, Cl or F, preferably Cl, or if $R^9$, $R^{10}$, $R^{12}$ and $R^{13}$ correspond to H, $R^{11}$ is chosen from $CF_3$, $CF_2H$, Cl or F, preferably from F, or if $R^{10}$, $R^{11}$ and $R^{12}$ correspond to H, one of $R^9$ or $R^{13}$ also corresponds to H, while the other is chosen from OH, $OC_2H_5$ or $OC_3H_7$.

It is particularly preferable for the part process according to the invention if, for compounds according to formula I where $R^3$=H and $R^2 \neq H$, these are in the configurations Ia or Ib

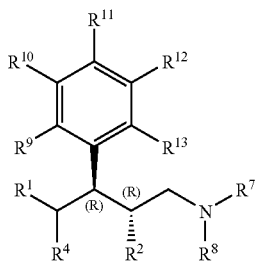

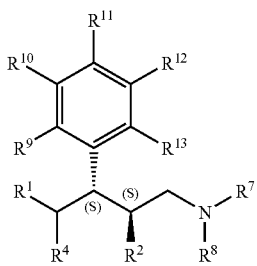

It is particularly preferable for the part process according to the invention if, for compounds according to formula III where $R^3=H$, $R^2\neq H$, $R^4=H$ and $R^1\neq H$, these are in the configurations IIIa or IIIb

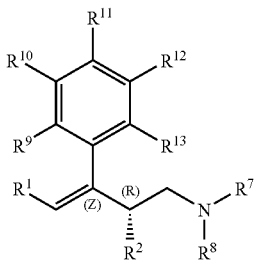

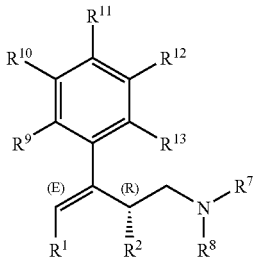

or for compounds according to formula III where $R^3=H$, $R^2\neq H$, $R^4=H$ and $R^1\neq H$, these are in the configurations IIIc or IIId

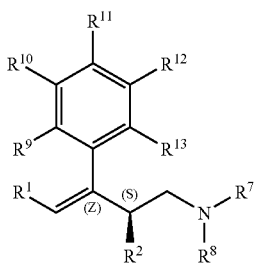

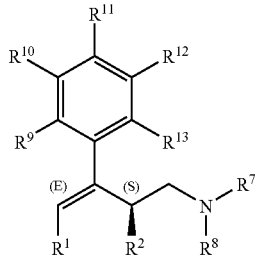

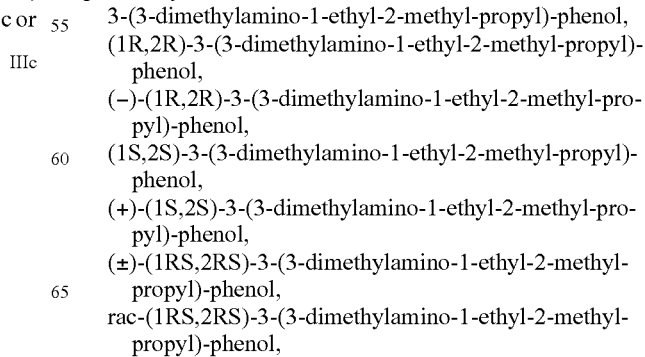

It is particularly preferable for the part process according to the invention if, for the compound/compounds according to formula I, at least one of these, preferably as the free base or as the hydrochloride, is chosen from the following group:

3-(3-dimethylamino-1-ethyl-2-methyl-propyl)-phenol,
(1R,2R)-3-(3-dimethylamino-1-ethyl-2-methyl-propyl)-phenol
(−)-(1R,2R)-3-(3-dimethylamino-1-ethyl-2-methyl-propyl)-phenol,
(1S,2S)-3-(3-dimethylamino-1-ethyl-2-methyl-propyl)-phenol
(+)-(1S,2S)-3-(3-dimethylamino-1-ethyl-2-methyl-propyl)-phenol
(±)-(1RS,2RS)-3-(3-dimethylamino-1-ethyl-2-methyl-propyl)-phenol
rac-(1RS,2RS)-3-(3-dimethylamino-1-ethyl-2-methyl-propyl)-phenol,
[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine,
(+)-(2S,3S)-[3-(3-methoxy-phenyl)-2-methyl-pentyl]-dimethylamine,
(±)-(2RS,3RS)-[3-(3-methoxy-phenyl)-2-methyl-pentyl]-dimethylamine,
rac(2RS,3RS)-[3-(3-methoxy-phenyl)-2-methyl-pentyl]-dimethylamine,
3{[3-(p-isopropyl-phenyl-carbamoyl)-oxy-phenyl]-2-methyl-pentyl}-dimethylamine,
(2R,3R)-{3 [3-(p-isopropyl-phenyl-carbamoyl)-oxy-phenyl]-2-methyl-pentyl}-dimethylamine,
(2S,3S)-{3 [3-(p-isopropyl-phenyl-carbamoyl)-oxy-phenyl]-2-methyl-pentyl}-dimethylamine,
(2SR,3SR)-{3 [3-(p-isopropyl-phenyl-carbamoyl)-oxy-phenyl]-2-methyl-pentyl}-dimethylamine preferably
3-(3-dimethylamino-1-ethyl-2-methyl-propyl)-phenol,
(1R,2R)-3-(3-dimethylamino-1-ethyl-2-methyl-propyl)-phenol,
(−)-(1R,2R)-3-(3-dimethylamino-1-ethyl-2-methyl-propyl)-phenol,
(1S,2S)-3-(3-dimethylamino-1-ethyl-2-methyl-propyl)-phenol,
(+)-(1S,2S)-3-(3-dimethylamino-1-ethyl-2-methyl-propyl)-phenol,
(±)-(1RS,2RS)-3-(3-dimethylamino-1-ethyl-2-methyl-propyl)-phenol,
rac-(1RS,2RS)-3-(3-dimethylamino-1-ethyl-2-methyl-propyl)-phenol,

[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine,
(+)-(2S,3S)-[3-(3-methoxy-phenyl)-2-methyl-pentyl]-dimethylamine, in particular
[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine,
(+)-(2S,3S)-[3-(3-methoxy-phenyl)-2-methyl-pentyl]-dimethylamine.

It is particularly preferable for the part process according to the invention if, for the compound/compounds according to formula III employed, at least one of these, preferably as the free base or as the hydrochloride, is chosen from the following group:
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl)-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol,
(Z,E)-(2S)-3-(3-dimethylamino-1-ethenyl-2-methyl-propyl)-phenol,
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine,
{3[3-(p-isopropyl-phenyl-carbamoyl)-oxy-phenyl]-2-methyl-pent-3-enyl}-dimethylamine,
(Z)-(2R)-{3[3-(p-isopropyl-phenyl-carbamoyl)-oxy-phenyl]-2-methyl-pent-3-enyl}-dimethylamine,
(E)-(2R)-{3[3-(p-isopropyl-phenyl-carbamoyl)-oxy-phenyl]-2-methyl-pent-3-enyl}-dimethylamine,
(Z,E)-(2R)-{3[3-(p-isopropyl-phenyl-carbamoyl)-oxy-phenyl]-2-methyl-pent-3-enyl}-dimethylamine,
(Z)-(2S)-{3[3-(p-isopropyl-phenyl-carbamoyl)-oxy-phenyl]-2-methyl-pent-3-enyl}-dimethylamine,
(E)-(2S)-{3[3-(p-isopropyl-phenyl-carbamoyl)-oxy-phenyl]-2-methyl-pent-3-enyl}-dimethylamine,
(Z,E)-(2S)-{3[3-(p-isopropyl-phenyl-carbamoyl)-oxy-phenyl]-2-methyl-pent-3-enyl}-dimethylamine, preferably
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl)-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol,
(Z,E)-(2S)-3-(3-dimethylamino-1-ethenyl-2-methyl-propyl)-phenol,
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine, in particular
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine, preferably
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine or
(Z,E)-(2R)-[3-(3-methoxy-phenyl)-2-methyl-pent-3-enyl]-dimethylamine, or
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl}-dimethylamine or
(Z,E)-(2S)-[3-(3-methoxy-phenyl)-2-methyl-pent-3-enyl]-dimethylamine.

It is particularly preferable for the part process according to the invention if a chiral center is present in the compound according to formula III employed, at position 2 according to formula III.

It is particularly preferable for the part process according to the invention if a chiral center is present in the compound according to formula I, at position 2 according to formula I.

It is particularly preferable for the part process according to the invention if the compound according to formula III employed is enantiomerically pure.

It is particularly preferable for the part process according to the invention if the compound according to formula III employed is diastereomerically pure.

It is particularly preferable for the part process according to the invention if the compound according to formula III employed is enantiomerically and diastereomerically pure.

It is particularly preferable for the part process according to the invention if the compound according to formula III employed is chosen from:
  (Z)-(2R)-[3-(3-methoxy-phenyl)-2-methyl-pent-3-enyl]-dimethylamine,
  (E)-(2R)-[3-(3-methoxy-phenyl)-2-methyl-pent-3-enyl]-dimethylamine or is a mixture of (Z)-(2R)-[3-(3-methoxy-phenyl)-2-methyl-pent-3-enyl]-dimethylamine and (E)-(2R)-[3-(3-methoxy-phenyl)-2-methyl-pent-3-enyl]-dimethylamine, or (Z,E)-(2R)-[3-(3-methoxy-phenyl)-2-methyl-pent-3-enyl]-dimethylamine.

It is particularly preferable for the part process according to the invention if the compound according to formula III employed is chosen from:
  (Z)-(2S)-[3-(3-methoxy-phenyl)-2-methyl-pent-3-enyl]-dimethylamine,
  (E)-(2S)-[3-(3-methoxy-phenyl)-2-methyl-pent-3-enyl]-dimethylamine or is a mixture of (Z)-(2S)-[3-(3-methoxy-phenyl)-2-methyl-pent-3-enyl]-dimethylamine and (E)-(2S)-[3-(3-methoxy-phenyl)-2-methyl-pent-3-enyl]-dimethylamine, or (Z,E)-(2S)-[3-(3-methoxy-phenyl)-2-methyl-pent-3-enyl]-dimethylamine.

It is particularly preferable for the part process according to the invention if the solvent is chosen from:
  $H_2O$ or alcohol or aqueous alcoholic or aqueous acidic solutions, preferably from aqueous acidic solutions.

It is particularly preferable for the part process according to the invention if the solvent is chosen from:
  $H_2O$ or ethanol or aqueous ethanolic solution or aqueous hydrochloric acid, preferably from aqueous hydrochloric acid.

It is particularly preferable for the part process according to the invention if the catalyst used comprises a noble metal, preferably platinum, gold or palladium, in particular palladium.

It is particularly preferable for the part process according to the invention if the catalyst used is palladium-on-active charcoal or palladium(II) chloride.

It is particularly preferable for the part process according to the invention if the catalyst used is palladium-on-active charcoal (1-10 wt. %, preferably 5 wt. %).

It is particularly preferable for the part process according to the invention if the temperature is kept between 20 and 40° C., preferably between 20 and 35, in particular 25° C.

It is preferable for the process according to the invention if, in step b), an inert gas atmosphere, in particular a nitrogen inert gas, is applied before the hydrogenation.

It is particularly preferable for the part process according to the invention if the hydrogenation takes place under a hydrogen pre-pressure of 3-10 bar, preferably 4-7 bar, in particular 5 bar and/or the hydrogenation step takes place under a hydrogen internal pressure of 0.5-3 bar, preferably 0.75-2 bar, in particular 1 bar.

It is particularly preferable for the part process according to the invention if the starting substances are highly dilute/diluted in the solvent at the start.

It is particularly preferable for the part process according to the invention if the compound according to formula III employed is dissolved in aqueous acid.

It is particularly preferable for the part process according to the invention if the compound according to formula III employed is dissolved in aqueous hydrochloric acid.

It is particularly preferable both for the process according to the invention and for the part process according to the invention if the products are precipitated in an organic solvent at the end of the process.

It is particularly preferable both for the process according to the invention and for the part process according to the invention if the products are precipitated with acid or acid gas, preferably hydrochloric acid or hydrochloric acid gas, in particular hydrochloric acid gas, at the end of the process.

It is particularly preferable both for the process according to the invention and for the part process according to the invention if the products are precipitated in an organic solvent with acid or acid gas, preferably hydrochloric acid or hydrochloric acid gas, in particular hydrochloric acid gas, at the end of the process.

General:

The elimination step (step a) of the process according to the invention

It has been found that in step a) of the process according to the invention formic acid, hydrochloric acid and hydrobromic acid are very particularly suitable for eliminating the tertiary OH group and achieving high yields.

If a chiral center is adjacent to the OH group, it is necessary to carry out the elimination regioselectively in order to prevent the chiral information from being lost. This is achieved astonishingly very well by the use of formic acid, hydrochloric acid and hydrobromic acid. In particular, the use of inexpensive hydrochloric acid, which can be converted into sodium chloride by neutralization after the end of the reaction, is preferred in this process. The regioselectivity of the elimination can be further influenced in a positive manner by modification of the reaction time, reaction temperature and concentration of the acid. High concentrations of the acid increasingly lead to the desired compounds. Particularly suitable reaction conditions are 36% hydrochloric acid over a reaction time of 5 hours and at a temperature of 55° C.

The Z isomers are obtained in good yields by crystallization of the compounds which have undergone elimination using hydrochloric acid gas in solvents. Small amounts of (Z,E)-dimethyl-(3-aryl-pent-2-enyl)-amine compounds, which are not desirable for this process, remain in solution or can be depleted by recrystallization.

The hydrogenation step (step b) in the process according to the invention and part process according to the invention This part process or step b) is of interest for compounds which have a chiral center in the vicinity of the OH group.

As is described above in the elimination step, it is possible to control the elimination such that the chiral center is involved in the elimination to only a small extent. By crystallization of the compounds which have undergone elimination, the (Z,E)-dimethyl-(3-aryl-pent-2-enyl)-amine compounds are depleted, so that no racemization on the adjacent C atom to the OH group can occur after the hydrogenation.

Astonishingly, the (Z,E)-dimethyl-(3-aryl-pent-2-enyl)-amine compounds cannot be hydrogenated on the double bond under the hydrogenation conditions described in this process, rather a loss of the dimethylamino group with secondary hydrogenations occurs in a first reaction.

For this reason it is possible to employ products which have undergone elimination in the hydrogenation without purification. Residual amounts of (Z,E)-dimethyl-(3-aryl-pent-2-enyl)-amine compounds contained in the crude products of the elimination are subjected to splitting off of dimethylamine during the elimination.

During the precipitation of the hydrogenated compounds with hydrochloric acid gas in organic solvents, the deaminated compounds cannot form salts, and therefore remain dissolved in the organic mother liquor.

As a result, astonishingly also no racemization can then occur, even if the starting substances for the hydrogenation step still contain residues of (Z,E)-dimethyl-(3-aryl-pent-2-enyl)-amine compounds.

The first hydrogenation was carried out in ethanol with the addition of palladium/C 10% and astonishingly a diastereomer ratio of 70:30 in favour of the diastereomers desired in this process, the (R,R)-(3-aryl-2-methyl-pentyl)-amines, was obtained.

It was found that at a high dilution of the starting substances in the solvent, the content of the desired diastereomer increases further up to 90%.

Astonishingly, by slow addition of the double bond component into the solvent, which has been initially introduced into the reaction vessel, with catalyst and hydrogen, a diastereomer concentration of 75% can be achieved.

An addition of catalytic amounts of hydrochloric acid also produces an increase in the desired diastereomer to 85% at a lower dilution.

The combination of dilution and acidification with aqueous hydrochloric acid produces an increase in the desired diastereomer to 90%.

In addition to palladium, palladium chloride can also be employed. Here also, the desired product is obtained in a good yield with a diastereomer excess of 70%. This process has the great advantage that the palladium obtained can be dissolved again in nitric acid after the hydrogenation and can be employed in the next hydrogenation almost without loss.

Combination of the two processes (process according to the invention)

It was particularly astonishing and satisfying that the elimination and hydrogenation can be carried out in a one-pot process.

Astonishingly, studies showed that the Z,E ratio of the (Z,E)-(2RS)-dimethyl-(3-aryl-2-methyl-pent-3-enyl)-amine compounds has no influence on the diastereomer ratio of the hydrogenated end products. It was therefore not necessary to isolate the pure Z products, which had undergone elimination, by crystallization.

The elimination was first carried out in aqueous hydrochloric acid, the palladium catalyst was subsequently added and the hydrogenation was then carried out. The desired (R,R)-diastereomer is obtained in an amount of 73%.

The invention is explained in the following with the aid of examples. These explanations are merely by way of example and do not limit the general inventive idea.

Certain embodiments of the present invention may be further understood by reference to the following specific examples. These examples and the terminology used herein are for the purpose of describing particular embodiments only and are not intended to be limiting.

EXAMPLES

For simplicity and illustrative purposes, the principles of the present invention are described by referring to various examples. One of ordinary skill in the art will readily recognize that the same principles are equally applicable to, and can be implemented in other forms, and that any such variation would be within those modifications that do not part from the true spirit and scope of the present invention. The invention is not limited in its application to the details of any particular formulation shown, since the invention is capable of other embodiments. The following examples are provided for illustrative purposes and do not and should not be understood to limit the claims appended hereto. The terminology used herein is for the purpose of description and not of limitation.

Example 1

15 kg (59.7 mol) (2S,3S)-1-dimethylamino-3-(3-methoxy-phenyl)-2-methyl-pentan-3-ol were initially introduced into a 100 l double-walled reaction unit with an electrical anchor stirrer, Pt100 temperature-measuring device and oil-based cooling/heating system at 20° C. and a stirring speed of 100 rpm, and 26.25 l 36 wt. % (308 mol) aqueous hydrochloric acid were added in the course of 10 min. The reaction mixture was heated to 50° C. in the course of 20 min and stirred at this temperature for 4-6 hours. Thereafter, the mixture was cooled to 25° C. and diluted with 13 l water. Approx. 32 l 32 wt. % (256 mol) sodium hydroxide solution were added at an internal temperature of 20° C., while cooling with a jacket temperature of 5° C., until a pH of 10-12.5 was reached. Thereafter, 22.5 l ethyl acetate were added and, after 10 min under stirring, the stirrer was switched off for the phase separation. The lower aqueous phase was drained off and the upper organic phase was distilled off at a maximum internal temperature of 50° C. under a vacuum to 10 mbar. The pale yellow oily residue which remained is the desired (Z,E)-(2R)-[3-(3-methoxy-phenyl)-2-methyl-pent-3-enyl]-dimethyl-amine. The yield is 13.6 kg (98% of theory) with an HPLC purity of 90% and a Z/E ratio of 70:30.

Example 2

15 kg (52.15 mol) (2S,3S)-1-dimethylamino-3-(3-methoxy-phenyl)-2-methyl-pentan-3-ol hydrochloride were initially introduced into a 100 l double-walled reaction unit with an electrical anchor stirrer, Pt100 temperature-measuring device and oil-based cooling/heating system at 20° C. and a stirring speed of 100 rpm, and 26.25 l 36 wt. % (308 mol) aqueous hydrochloric acid were added in the course of 10 min. The reaction mixture was heated to 50° C. in the course of 20 min and stirred at this temperature for 4-6 hours. Thereafter, the mixture was cooled to 25° C. and diluted with 13 l water. Approx. 32 l 32 wt. % (256 mol) sodium hydroxide solution were added at an internal temperature of 20° C., while cooling with a jacket temperature of 5° C., until a pH of 10-12.5 was reached. Thereafter, 22.5 l ethyl acetate were added and, after 10 min under stirring, the stirrer was switched off for the phase separation. The lower aqueous phase was drained off and the upper organic phase was distilled off at a maximum internal temperature of 50° C. under a vacuum to 10 mbar. The pale yellow oily residue which remained is the desired (Z,E)-(2R)-[3-(3-methoxy-phenyl)-2-methyl-pent-3-enyl]-dimethyl-amine. The yield is 11.9 kg (98% of theory) (54.4 mol) with an HPLC purity of 90% and a Z/E ratio of 70:30.

Example 3

15 kg (59.68 mol) of a 70:30 mixture of (2S,3S)-1-dimethylamino-3-(3-methoxy-phenyl)-2-methyl-pentan-3-ol and (2S,3R)-1-dimethylamino-3-(3-methoxy-phenyl)-2-methyl-pentan-3-ol were initially introduced into a 100 l double-walled reaction unit with an electrical anchor stirrer, Pt100 temperature-measuring device and oil-based cooling/heating system at 20° C. and a stirring speed of 100 rpm, and 26.25 l 36 wt. % (307.9 mol) aqueous hydrochloric acid were added in the course of 10 min. The reaction mixture was heated to 50° C. in the course of 20 min and stirred at this temperature for 4-6 hours. Thereafter, the mixture was cooled to 25° C. and diluted with 13 l water. Approx. 32 l 32 wt. % sodium hydroxide solution (256 mol) were added at an internal temperature of 20° C., while cooling with a jacket temperature of 5° C., until a pH of 10-12.5 was reached. Thereafter, 22.5 l ethyl acetate were added and, after 10 min under stirring, the stirrer was switched off for the phase separation. The lower aqueous phase was drained off and the upper organic phase was distilled off at a maximum internal temperature of 50° C. under a vacuum to 10 mbar. The pale yellow oily residue which remained is the desired (Z,E)-(2R)-[3-(3-methoxy-phenyl)-2-methyl-pent-3-enyl]-dimethyl-amine. The yield is 13.6 kg (58.3 mol) (98% of theory) with an HPLC purity of 90% and a Z/E ratio of 70:30.

Example 4

15 kg (59.68 mol) of a mixture of (2S,3S)-1-dimethylamino-3-(3-methoxy-phenyl)-2-methyl-pentan-3-ol (35 wt. %), (2R,3R)-1-dimethylamino-3-(3-methoxy-phenyl)-2-methyl-pentan-3-ol (35 wt. %), (2R,3S)-1-dimethylamino-3-(3-methoxy-phenyl)-2-methyl-pentan-3-ol (15 wt. %) and (2S,3R)-1-dimethylamino-3-(3-methoxy-phenyl)-2-methyl-pentan-3-ol (15 wt. %) were initially introduced into a 100 l double-walled reaction unit with an electrical anchor stirrer, Pt100 temperature-measuring device and oil-based cooling/heating system at 20° C. and a stirring speed of 100 rpm, and 26.25 l 36 wt. % aqueous hydrochloric acid were added in the course of 10 min. The reaction mixture was heated to 50° C. in the course of 20 min and stirred at this temperature for 4-6 hours. Thereafter, the mixture was cooled to 25° C. and diluted with 13 l water. Approx. 32 l 32 wt. % sodium hydroxide solution were added at an internal temperature of 20° C., while cooling with a jacket temperature of 5° C., until a pH of 10-12.5 was reached. Thereafter, 22.5 l ethyl acetate were added and, after 10 min under stirring, the stirrer was switched off for the phase separation. The lower aqueous phase was drained off and the upper organic phase was distilled off at a maximum internal temperature of 50° C. under a vacuum to 10 mbar. The pale yellow oily residue which remained is the desired mixture of (Z,E)-(2R)-[3-(3-methoxy-phenyl)-2-methyl-pent-3-enyl]-dimethyl-amine and (Z,E)-(2S)-[3-(3-methoxy-phenyl)-2-methyl-pent-3-enyl]-dimethyl-amine. The yield is 13.6 kg (98% of theory) with an HPLC purity of 90% and a Z/E ratio of 70:30.

Example 5

28.7 g (0.1 mol) (2S,3S)-1-dimethylamino-3-(3-methoxy-phenyl)-2-methyl-pentan-3-ol hydrochloride were initially introduced into a 250 ml three-necked flask with a thermometer, mechanical compressed air stirrer, reflux condenser and oil bath heating, and 150 ml formic acid were added. The mixture was boiled under reflux for 4 hours. It was cooled and poured into a 500 ml round-bottomed flask and the formic acid was distilled off on a Büchi 5 l rotary evaporator at 60° C. to a pressure of 10 mbar. 150 ml ethyl acetate and 100 ml water were added to the oily residue. A pH of 11 was established with 33 wt. % sodium hydroxide solution, the phases were separated and the ethyl acetate was distilled off on a rotary evaporator at 60° C. to a pressure of 10 mbar. The oily residue consists of (Z,E)-(2R)-[3-(3-methoxy-phenyl)-2-methyl-pent-3-enyl]-dimethyl-amine with a GC purity of 92%, a Z/E ratio of 2.2:1 and a yield of 21.0 g (90% of theory). In the purity analysis, 0.37% of unreacted starting substance and 2.01% of (Z,E)-[3-(3-methoxy-phenyl)-2-methyl-pent-2-enyl]-dimethyl-amine hydrochloride were also found.

Example 6

28.7 g (0.1 mol) (2S,3S)-1-dimethylamino-3-(3-methoxy-phenyl)-2-methyl-pentan-3-ol hydrochloride were initially introduced into a 250 ml three-necked flask with a thermometer, mechanical compressed air stirrer, reflux condenser and oil bath heating, and 75 ml 47 wt. % hydrobromic acid were added. The mixture was heated at 50° C. for 1 hour. It was cooled to 20° C. and a pH of 11 was established with 33 wt. % sodium hydroxide solution at 20° C., while cooling. 150 ml ethyl acetate were added, the mixture was stirred for 10 min, the stirrer was switched off, the phases were separated and the ethyl acetate was distilled off on a rotary evaporator at 60° C. to a pressure of 10 mbar. The oily residue consists of (Z,E)-(2R)-[3-(3-methoxy-phenyl)-2-methyl-pent-3-enyl]-dimethyl-amine with a GC purity of 93%, a Z/E ratio of 4:1 and a yield of 21 g (90% of theory). In the purity analysis, 1.52% of unreacted starting substance and 2.1% of (Z,E)-[3-(3-methoxy-phenyl)-2-methyl-pent-2-enyl]-dimethyl-amine hydrochloride were also found.

Example 7

28.7 g (0.1 mol) (2R,3R)-1-dimethylamino-3-(3-methoxy-phenyl)-2-methyl-pentan-3-ol hydrochloride were initially introduced into a 250 ml three-necked flask with a thermometer, mechanical compressed air stirrer, reflux condenser and oil bath heating, and 75 ml 47 wt. % hydrobromic acid were added. The mixture was heated at 35° C. for 4 hours. It was cooled to 20° C. and a pH of 11 was established with 33 wt. % sodium hydroxide solution at 20° C., while cooling. 150 ml ethyl acetate were added, the mixture was stirred for 10 min, the stirrer was switched off, the phases were separated and the ethyl acetate was distilled off on a rotary evaporator at 60° C. to a pressure of 10 mbar. The oily residue consists of (Z,E)-(2S)-[3-(3-methoxy-phenyl)-2-methyl-pent-3-enyl]-dimethyl-amine with a GC purity of 90.5%, a Z/E ratio of 2.9:1 and a yield of 21 g (90% of theory). In the purity analysis, 4.92% of unreacted starting substance and 1.5% of (Z,E)-[3-(3-methoxy-phenyl)-2-methyl-pent-2-enyl]-dimethyl-amine hydrochloride were also found.

Example 8

28.7 g (0.1 mol) (2R,3R)-1-dimethylamino-3-(3-methoxy-phenyl)-2-methyl-pentan-3-ol hydrochloride were initially introduced into a 250 ml three-necked flask with a thermometer, mechanical compressed air stirrer, reflux condenser and oil bath heating, and 75 ml 47 wt. % hydrobromic acid were added. The mixture was heated at 35° C. for 4 hours. It was cooled to 20° C. and a pH of 11 was established with 33 wt. % sodium hydroxide solution at 20° C., while cooling. 150 ml ethyl acetate were added, the mixture was stirred for 10 min, the stirrer was switched off, the phases were separated and the ethyl acetate was distilled off on a rotary evaporator at 60° C. to a pressure of 10 mbar. The oily residue consists of (Z,E)-(2S)-[3-(3-methoxy-phenyl)-2-methyl-pent-3-enyl]-dimethyl-amine with a GC purity of 90.5%, a Z/E ratio of 2.9:1 and a yield of 21 g (90% of theory). In the purity analysis, 4.92% of unreacted starting substance and 1.5% of (Z,E)-[3-(3-methoxy-phenyl)-2-methyl-pent-2-enyl]-dimethyl-amine hydrochloride were also found.

Example 9

28.7 g (0.1 mol) (2S,3R)-1-dimethylamino-3-(3-methoxy-phenyl)-2-methyl-pentan-3-ol hydrochloride were initially introduced into a 250 ml three-necked flask with a thermometer, mechanical compressed air stirrer, reflux condenser and oil bath heating, and 150 ml aqueous 36 wt. % hydrochloric acid were added. The mixture was heated at 55° C. for 19 hours. It was cooled to 20° C. and a pH of 11 was established with 33 wt. % sodium hydroxide solution at 20° C., while cooling. 150 ml ethyl acetate were added, the mixture was stirred for 10 min, the stirrer was switched off, the phases were separated and the ethyl acetate was distilled off on a rotary evaporator at 60° C. to a pressure of 10 mbar. The oily residue consists of (Z,E)-(2R)-[3-(3-methoxy-phenyl)-2-methyl-pent-3-enyl]-dimethyl-amine with a GC purity of 40%, a Z/E ratio of 3.5:1 and a yield of 21 g (90% of theory). In the purity analysis, no starting substance and 40% of (Z,E)-[3-(3-methoxy-phenyl)-2-methyl-pent-2-enyl]-dimethyl-amine was found.

Example 10

28.7 g (0.1 mol) (2S,3R)-1-dimethylamino-3-(3-methoxy-phenyl)-2-methyl-pentan-3-ol hydrochloride were initially introduced into a 250 ml three-necked flask with a thermometer, mechanical compressed air stirrer, reflux condenser and oil bath heating, and 150 ml aqueous 36 wt. % hydrochloric acid were added. The mixture was heated at 100° C. for 1 hour. It was cooled to 20° C. and a pH of 11 was established with 33 wt. % sodium hydroxide solution at 20° C., while cooling. 150 ml ethyl acetate were added, the mixture was stirred for 10 min, the stirrer was switched off, the phases were separated and the ethyl acetate was distilled off on a rotary evaporator at 60° C. to a pressure of 10 mbar. The oily residue consists of (Z,E)-(2R)-[3-(3-methoxy-phenyl)-2-methyl-pent-3-enyl]-dimethyl-amine with a GC purity of 86%, a Z/E ratio of 6.5:1 and a yield of 21 g (90% of theory). In the purity analysis, no starting substance and 8.5% of (Z,E)-[3-(3-methoxy-phenyl)-2-methyl-pent-2-enyl]-dimethyl-amine was found.

Example 11

10 kg (42.85 mol) (Z,E)-(2R)-[3-(3-methoxy-phenyl)-2-methyl-pent-3-enyl]-dimethyl-amine were dissolved in 25 l ethanol abs. denat. in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 25° C. and a stirrer speed of 850±150 rpm. The reaction unit was rendered inert with nitrogen. A suspension of 750 g palladium-on-active charcoal (5 wt. %) in 5 l ethanol was added to the solution under nitrogen as an inert gas. After the reaction unit had been rendered inert again, hydrogenation was carried out with a hydrogen pre-pressure of 5 bar and an internal pressure of 1 bar until the uptake of hydrogen had ended. When the reaction had ended the unit was rendered inert again with nitrogen and the reaction mixture was filtered over a single-layer filter covered with filter earth in order to remove the catalyst. The clear filtrate was concentrated to constant weight on a rotary evaporator under a continuously reduced pressure. The clear oil which remains is a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 9.96 kg (42.3 mol) (99% of theory) with a GC purity of 90%. The diastereomer ratio (R,R enantiomer to R,S enantiomer) is 2.8:1.

Example 12

0.8 kg (3.43 mol) (Z,E)-(2R)-[3-(3-methoxy-phenyl)-2-methyl-pent-3-enyl]-dimethyl-amine was dissolved in 25 l ethanol abs. denat. in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 25° C. and a stirrer speed of 850±150 rpm. The reaction unit was rendered inert with nitrogen. A suspension of 60 g palladium-on-active charcoal (5 wt. %) in 5 l ethanol was added to the solution under nitrogen as an inert gas. After the reaction unit had been rendered inert again, hydrogenation was carried out with a hydrogen pre-pressure of 5 bar and an internal pressure of 1 bar until the uptake of hydrogen had ended. When the reaction had ended the unit was rendered inert again with nitrogen and the reaction mixture was filtered over a single-layer filter covered with filter earth in order to remove the catalyst. The clear filtrate was concentrated to constant weight on a rotary evaporator under a continuously reduced pressure. The clear oil which remained was a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 0.80 kg (99% of theory) with a GC purity of 94%. The diastereomer ratio (R,R enantiomer to R,S enantiomer) is 5.9:1.

Example 13

5 kg (21.43 mol) (Z,E)-(2R)-[3-(3-methoxy-phenyl)-2-methyl-pent-3-enyl]-dimethyl-amine were dissolved in 13 l ethanol abs. denat. in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 25° C. and a stirrer speed of 850±150 rpm. The reaction unit was rendered inert with nitrogen.

375 g palladium-on-active charcoal (5 wt. %) were suspended in 0.675 kg 32 wt. % hydrochloric acid under nitrogen as an inert gas The catalyst suspension was added to the reaction solution, while stirring. After the reaction unit had been rendered inert again, hydrogenation was carried out with a hydrogen pre-pressure of 5 bar and an internal pressure of 1 bar until the uptake of hydrogen had ended.

When the reaction had ended the unit was rendered inert with nitrogen and the reaction mixture was filtered over a single-layer filter covered with filter earth in order to remove the catalyst. The slightly cloudy filtrate was concentrated to constant weight on a rotary evaporator under a continuously reduced pressure. The white solid suspension which remained was taken up in 10 l ethyl acetate, 3.7 l 10 wt. % sodium hydroxide solution were added at 20° C. and a pH of 10-12 was established. The lower aqueous phase was separated off and discarded. The upper organic phase was concentrated to constant weight in a rotary evaporator at 45-50° C. under a continuously reduced pressure. The clear oil which remains is a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 4.5 kg (90% of theory) with a GC purity of 90%. The diastereomer ratio (R,R enantiomer to R,S enantiomer) is 5.5:1 after isolation of the base.

Example 14

5 kg (21.43 mol) (Z,E)-(2R)-[3-(3-methoxy-phenyl)-2-methyl-pent-3-enyl]-dimethyl-amine were dissolved in 12.5 l ethanol abs. denat. in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 25° C. and a stirrer speed of 850±150 rpm. The reaction unit was rendered inert with nitrogen. A suspension of 1.87 g palladium-on-active charcoal (1 wt. %) in 2.5 l ethanol and 630 g water was added to the solution under nitrogen as an inert gas. After the reaction unit had been rendered inert again, hydrogenation was carried out with a hydrogen pre-pressure of 5 bar and an internal pressure of 1 bar until the uptake of hydrogen had ended.

When the reaction had ended the unit was rendered inert with nitrogen and the reaction mixture was filtered over a single-layer filter covered with filter earth in order to remove the catalyst. The clear filtrate was concentrated to constant weight on a rotary evaporator under a continuously reduced pressure. The clear oil which remains is a mixture of the desired (−)(2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 4.90 kg (98% of theory) with a GC purity of 89%. The diastereomer ratio (R,R enantiomer to R,S enantiomer) is 2.7:1 after isolation of the base.

Example 15

5 kg (21.43 mol) (Z,E)-(2R)-[3-(3-methoxy-phenyl)-2-methyl-pent-3-enyl]-dimethyl-amine were dissolved in 12.5 l ethanol abs. denat. in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 25° C. and a stirrer speed of 850±150 rpm. The reaction unit was rendered inert with nitrogen. A suspension of 0.19 kg palladium-on-active charcoal (10 wt. %) in 2.5 l ethanol and 630 g water was added to the solution under nitrogen as an inert gas. After the reaction unit had been rendered inert again, hydrogenation was carried out with a hydrogen pre-pressure of 5 bar and an internal pressure of 1 bar until the uptake of hydrogen had ended.

When the reaction had ended the unit was rendered inert with nitrogen and the reaction mixture was filtered over a single-layer filter covered with filter earth in order to remove the catalyst. The clear filtrate was concentrated to constant weight on a rotary evaporator under a continuously reduced pressure. The clear oil which remains is a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 4.90 kg (98% of theory) with a GC purity of 87%. The diastereomer ratio (R,R enantiomer to R,S enantiomer) is 3.0:1 after isolation of the base.

Example 16

5.76 kg (22.9 mol) (2S,3R)-1-dimethylamino-3-(3-methoxy-phenyl)-2-methyl-pentan-3-ol were initially introduced into a 100 l double-walled reaction unit with an electrical anchor stirrer, Pt100 temperature-measuring device and oil-based cooling/heating system at 20° C. and a stirring speed of 100 rpm, and 12.22 l 36 wt. % aqueous hydrochloric acid were added in the course of 10 min. The reaction mixture was heated to 70° C. in the course of 30 min and stirred at this temperature for 1 hour.

The solution was then cooled to 20° C. and 10 l 25 wt. % sodium hydroxide solution and 5 kg NaCl were added. A white suspension formed. The suspension was transferred to the hydrogenation apparatus.

In a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller, a suspension of 0.230 kg palladium-on-active charcoal (1 wt. %) in 2.5 l water was added to the suspension under nitrogen as an inert gas and the components were mixed at 25° C. and a stirrer speed of 850±150 rpm. The reaction unit was rendered inert with nitrogen. Hydrogenation was then carried out with a hydrogen pre-pressure of 5 bar and an internal pressure of 1 bar until the uptake of hydrogen had ended.

When the reaction had ended the unit was rendered inert with nitrogen and the reaction mixture was filtered over a single-layer filter covered with filter earth in order to remove the catalyst. 18 l 32 wt. % sodium hydroxide solution were added to the clear filtrate and a pH of 11-12 was established, a precipitate occurring. tert-Butyl methyl ether was added and a phase separation was carried out. The organic phase was concentrated to constant weight on a rotary evaporator under a continuously reduced pressure. The clear oil which remains is a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 4.10 kg (76% of theory) with a GC purity of 90%. The diastereomer ratio (R,R enantiomer to R,S enantiomer) is 2.7:1 after isolation of the base.

Example 17

5.42 kg (20 mol) (Z,E)-(2R)-[3-(3-methoxy-phenyl)-2-methyl-pent-3-enyl]-dimethyl-amine hydrochloride were dissolved in 25 l water in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 45° C. and a stirrer speed of 850±150 rpm. The reaction unit was rendered inert with nitrogen. A suspension of 0.086 kg palladium-on-active charcoal (5 wt. %) in 2.5 l water was added to the solution under nitrogen as an inert gas. After the reaction unit had been rendered inert again, hydrogenation was carried out with a hydrogen pre-pressure of 5 bar and an internal pressure of 1 bar until the uptake of hydrogen had ended. When the reaction had ended the unit was rendered inert with nitrogen and the reaction mixture was filtered over a single-layer filter covered with filter earth in order to remove the catalyst. 1.5 l 10 wt. % sodium hydroxide solution were added to the clear filtrate, a precipitate occurring. tert-Butyl methyl ether was added and a phase separation was carried out. The organic phase was concentrated to constant weight on a rotary evaporator under a continuously reduced pressure. The clear oil which remains is a mixture of the desired (2R, 3R)-[3-(3-methoxy-phenyl)-2-methyl-pentyl]dimethylamine and (2R,3S)-[3-(3-methoxy-phenyl)-2-methyl-pentyl]dimethylamine. The yield is 4.10 kg (87% of theory) with a GC purity of 85%. The diastereomer ratio (R,R enantiomer to R,S enantiomer) is 2.6:1 after isolation of the base.

Example 18

0.8 kg (3.44 mol) (Z,E)-(2R)-[3-(3-methoxy-phenyl)-2-methyl-pent-3-enyl]-dimethyl-amine were dissolved in 25 l ethanol abs. denat. in a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller at 25° C. and a stirrer speed of 850±150 rpm. The reaction unit was rendered inert with nitrogen.

60 g palladium-on-active charcoal (5 wt. %) were suspended in 0.675 kg 32 wt. % hydrochloric acid under nitrogen as an inert gas. The catalyst suspension was added to the reaction solution, while stirring. After the reaction unit had been rendered inert again, hydrogenation was carried out with a hydrogen pre-pressure of 5 bar and an internal pressure of 1 bar until the uptake of hydrogen had ended.

When the reaction had ended the unit was rendered inert again with nitrogen and the reaction mixture was filtered over a single-layer filter covered with filter earth in order to remove the catalyst. The clear filtrate was concentrated to constant weight on a rotary evaporator under a continuously reduced pressure. The clear oil which remained was a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 0.80 kg (99% of theory) with a GC purity of 94%. The diastereomer ratio (R,R enantiomer to R,S enantiomer) is 8.5:1.

Example 19

5.76 kg (22.9 mol) (2S,3R)-1-dimethylamino-3-(3-methoxy-phenyl)-2-methyl-pentan-3-ol were initially introduced into a 100 l double-walled reaction unit with an electrical anchor stirrer, Pt100 temperature-measuring device and oil-based cooling/heating system at 20° C. and a stirring speed of 100 rpm, and 12.22 l 36 wt. % aqueous hydrochloric acid were added in the course of 10 min. The reaction mixture was heated to 70° C. in the course of 30 min and stirred at this temperature for 1 hour.

The solution was then cooled to 20° C. and 10 l 25 wt. % sodium hydroxide solution and 5 kg NaCl were added. A white suspension formed. The suspension was transferred to the hydrogenation apparatus.

In a coolable and heatable 50 l double-walled hydrogenation apparatus with a permanently attached cover plate with a hydrogen and nitrogen feed, electrical gassing stirrer, baffle, PT 100 temperature-measuring device, inspection glass, hand hole and "Büchi bpc" gas controller, a solution of 0.288 kg palladium(II) chloride in 2.5 l water was added to the suspension under nitrogen as an inert gas and the components were mixed at 25° C. and a stirrer speed of 850±150 rpm. The reaction unit was rendered inert with nitrogen. Hydrogenation was then carried out with a hydrogen pre-pressure of 5 bar and an internal pressure of 1 bar until the uptake of hydrogen had ended.

When the reaction had ended the unit was rendered inert with nitrogen and the reaction mixture was filtered over a single-layer filter covered with filter earth in order to remove the catalyst. 18 l 32 wt. % sodium hydroxide solution were added to the clear filtrate and a pH of 11-12 was established, a precipitate occurring. tert-Butyl methyl ether was added and a phase separation was carried out. The organic phase was concentrated to constant weight on a rotary evaporator under a continuously reduced pressure. The clear oil which remains is a mixture of the desired (2R,3R)-[3-(3-methoxy-phenyl)-2-methyl-pentyl]dimethylamine and (2R,3S)-[3-(3-methoxy-phenyl)-2-methyl-pentyl]dimethylamine. The yield is 4.10 kg (76% of theory) with a GC purity of 90%. The diastereomer ratio (R,R enantiomer to R,S enantiomer) is 10:1 after isolation of the base.

Example 17

GC Method for the Analysis

Sample Preparation:

tert-BME is added to the sample material. Hydrochlorides are liberated with Dowex MWA-1 to give the base. The clear organic phase is injected.

Gas Chromatography Conditions:

| | |
|---|---|
| Capillary column | 6% cyanopropyl-phenyl-94% dimethylpolysiloxane e.g. OPTIMA 1301-DF 1.0 µm; 30 m × 0.32 mm i.d. |
| Carrier gas: | Helium |
| Pre-pressure | 70 kPa; Split: 20 ml/min |
| Oven temperature program | Initial 160° C./5 min Rate 5° C./min 190° C./9 min Rate 10° C./min 150° C./14 minutes |
| Detector | FID |
| Detector temperature | 260° C. |
| Injector temperature | 250° C. |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed:

1. A method for the preparation of a substituted 3-aryl-butyl-amine compound corresponding to formula I

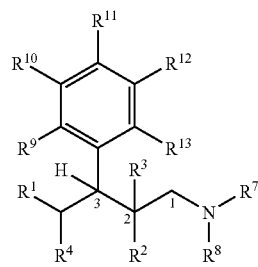

wherein
R$^1$ is chosen from H, C$_{1-3}$-alkyl, which is branched or unbranched, saturated or unsaturated, unsubstituted or mono- or polysubstituted,
R$^2$ and R$^3$ in each case independently of one another are chosen from H or C$_{1-4}$-alkyl, which is branched or unbranched, saturated or unsaturated, unsubstituted or mono- or polysubstituted,
or
R$^2$ and R$^3$ together form a saturated C$_{4-7}$-cycloalkyl radical, which is unsubstituted or mono- or polysubstituted,
R$^4$ is chosen from H, C$_{1-3}$-alkyl, which is branched or unbranched, saturated or unsaturated, unsubstituted or mono- or polysubstituted,
R$^7$ and R$^8$ in each case independently of one another are chosen from H or C$_{1-3}$-alkyl, which is branched or unbranched, saturated or unsaturated, unsubstituted or mono- or polysubstituted,
R$^9$ to R$^{13}$ in each case independently of one another are chosen from H, F, Cl, Br, I, CH$_2$F, CHF$_2$, CF$_3$, OH, SH, OR$^{14}$, OCF$_3$, SR$^{14}$, NR$^{17}$R$^{18}$, SOCH$_3$, SOCF$_3$; SO$_2$CH$_3$, SO$_2$CF$_3$, CN, COOR$^{14}$, NO$_2$, CONR$^{17}$R$^{18}$; C$_{1-6}$-alkyl, which is branched or unbranched, saturated or unsaturated, unsubstituted or mono- or polysubstituted; phenyl, which is unsubstituted or mono- or polysubstituted;
where R$^{14}$ is chosen from C$_{1-6}$-alkyl; pyridyl, thienyl, thiazolyl, phenyl, benzyl or phenethyl, in each case unsubstituted or mono- or polysubstituted; PO(O—C$_{1-4}$-alkyl)$_2$, CO(OC$_{1-5}$-alkyl), CONH—C$_6$H$_4$-(C$_{1-3}$-alkyl), CO(C$_{1-5}$-alkyl), CO—CHR$^{17}$—NHR$^{18}$, CO—C$_6$H$_4$—R$^{15}$, where R$^{15}$ is ortho-OCOC$_{1-3}$-alkyl or meta- or para-CH$_2$N(R$^{16}$)$_2$, where R$^{16}$ is C$_{1-4}$-alkyl or 4-morpholino, wherein in the radicals R$^{14}$, R$^{15}$ and R$^{16}$ the alkyl groups can be branched or unbranched, saturated or unsaturated, unsubstituted or mono- or polysubstituted;
where R$^{17}$ and R$^{18}$ in each case independently of one another are chosen from H; C$_{1-6}$-alkyl, which is branched or unbranched, saturated or unsaturated, unsubstituted or mono- or polysubstituted; phenyl, benzyl or phenethyl, in each case unsubstituted or mono- or polysubstituted,
or
R$^9$ and R$^{10}$ or R$^{10}$ and R$^{11}$ together form an OCH$_2$O, OCH$_2$CH$_2$O, OCH═CH, CH═CHO, CH═C(CH$_3$)O, OC(CH$_3$)═CH, (CH$_2$)$_4$ or OCH═CHO ring,
in each case in the form of one of its stereoisomers, its racemates or in the form of a mixture of stereoisomers, in any desired mixing ratio, or in each case in the form of a physiologically acceptable salt, or in each case in the form of a solvate,
said method comprising the step of:
hydrogenating a substituted 3-aryl-but-3-enyl-amine compound corresponding to formula III in the presence of a platinum or palladium catalyst and hydrogen to produce a substituted 3-aryl-butyl-amine compound corresponding to formula I

III

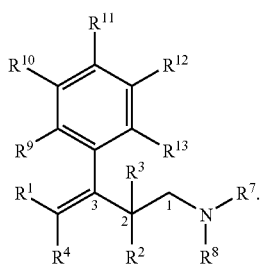

2. A method according to claim 1, further comprising an initial step of:
reacting a 1-amino-3-aryl-butan-3-ol compound corresponding to formula II

II

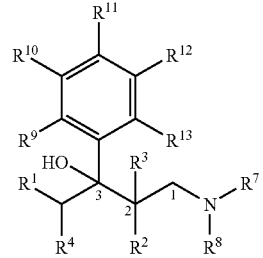

with an acid to produce a substituted 3-aryl-but-3-enyl-amine compound corresponding to formula III.

3. A method according to claim 2, wherein for compounds according to formula I, formula II and formula III, R$^4$ is chosen from H and CH$_3$.

4. A method according to claim 2, wherein for compounds according to formula I, formula II and formula III, R$^1$ is chosen from C$_{1-3}$-alkyl, which is saturated or unsaturated, substituted or unsubstituted, branched or unbranched.

5. A method according to claim 2, wherein for compounds according to formula I, formula II and formula III, R$^4$ is chosen from H and CH$_3$, and R$^1$ is chosen from C$_{1-3}$-alkyl, which is saturated or unsaturated, substituted or unsubstituted, branched or unbranched.

6. A method according to claim 2, wherein for compounds according to formula I, formula II and formula III, R$^7$ and R$^8$ in each case independently of one another are chosen from H and CH$_3$.

7. A method according to claim 2, wherein for compounds according to formula I, formula II and formula III, R$^1$ is chosen from from CH$_3$, C$_2$H$_5$, i-propyl and n-propyl.

8. A method according to claim 2, wherein for compounds according to formula I, formula II and formula III, R$^2$ and R$^3$ independently of one another are chosen from H and C$_{1-4}$-alkyl, which is saturated and unsubstituted, branched or unbranched.

9. A method according to claim 2, wherein for compounds according to formula I, formula II and formula III, R$^2$ and R$^3$ independently of one another are chosen from H, CH$_3$, C$_2$H$_5$, i-propyl and t-butyl.

10. A method according to claim 2, wherein for compounds according to formula I, formula II and formula III, R$^3$═H and R$^2$ is not H.

11. A method according to claim 2, wherein for compounds according to formula I, formula II and formula III, R$^2$ and R$^3$ together form a C$_{5-6}$-cycloalkyl radical, which is saturated or unsaturated, unsubstituted or mono- or polysubstituted.

12. A method according to claim 2, wherein for compounds according to formula I, formula II and formula III, R$^2$ and R$^3$ together form cyclohexyl.

13. A method according to claim 2, wherein for compounds according to formula I, formula II and formula III,
R$^9$ to R$^{13}$ independently of one another are chosen from H, Cl, F, OH, CF$_2$H, CF$_3$ or C$_{1-4}$-alkyl, which is saturated and unsubstituted, branched or unbranched; OR$^{14}$ or SR$^{14}$, where R$^{14}$ is chosen from C$_{1-3}$-alkyl, which is saturated and unsubstituted, branched or unbranched and 3 or 4 of the radicals R$^9$ to R$^{13}$ must correspond to H; or
R$^{12}$ and R$^{11}$ form a 3,4-OCH═CH ring.

14. A method according to claim 2, wherein for compounds according to formula I, formula II and formula III $R^1$ is chosen from
C$_{1-3}$-alkyl, which is saturated and unsubstituted, branched or unbranched;
and
$R^2$ and $R^3$ independently of one another are chosen from H, C$_{1-4}$-alkyl, which is saturated and unsubstituted, branched or unbranched;
or
$R^2$ and $R^3$ together form a C$_{5-6}$-cycloalkyl radical, which is saturated or unsaturated, unsubstituted or mono- or polysubstituted,
and
$R^4$ is H,
and
$R^7$ and $R^8$ in each case independently of one another are chosen from
H and CH$_3$,
and
$R^9$ to $R^{13}$, independently of one another, are chosen from H, Cl, F, OH, CF$_2$H, CF$_3$ or C$_{1-4}$-alkyl, which is saturated and unsubstituted, branched or unbranched; OR$^{14}$ or SR$^{14}$, where R$^{14}$ is chosen from C$_{1-3}$-alkyl, which is saturated and unsubstituted, branched or unbranched; and
where 3 or 4 of the radicals R$^9$ to R$^{13}$ must correspond to H.

15. A method according to claim 1, wherein for compounds according to formula I where $R^3$=H and $R^2$ is not H the compounds are in the configurations Ia or Ib Ia
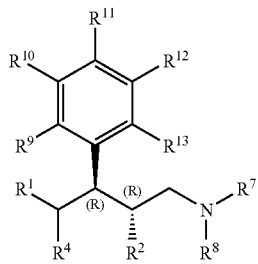

Ib
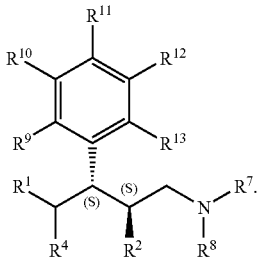

16. A method according to claim 2, wherein for compounds according to formula II where $R^3$=H and $R^2$ is not H the compounds are in the configurations IIa or IIb IIa
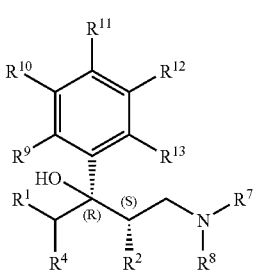

IIb
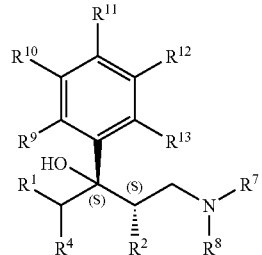

or in the configurations IIc and IId

IIc
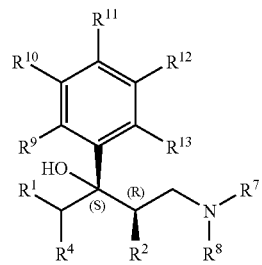

IId
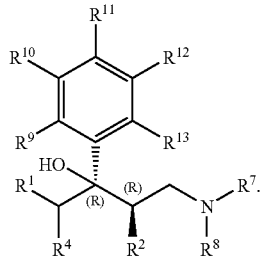

17. A method according to claim 1, wherein for compounds according to formula III where $R^3$=H, $R^2$ is not H, $R^4$=H and $R^1$ is not H these compounds are in the configurations IIIa or IIIb IIIa
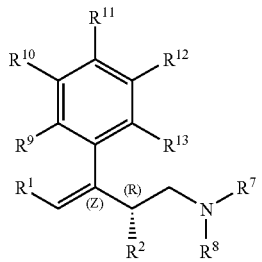

IIIb
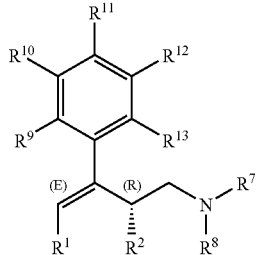

or for compounds according to formula III where $R^3$=H, $R^2$ is not H, $R^4$=H and $R^1$ is not H these are in the configurations IIIc or IIId

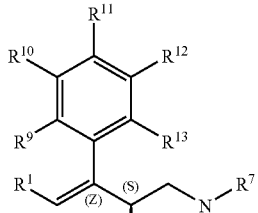

IIIc

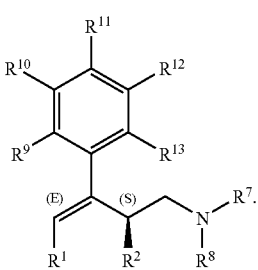

IIId

18. A method according to claim 1, wherein the compound according to formula I is selected from the group consisting of:
3-(3-dimethylamino-1-ethyl-2-methyl-propyl)-phenol,
(1R,2R)-3-(3-dimethylamino-1-ethyl-2-methyl-propyl)-phenol
(−)-(1R,2R)-3-(3-dimethylamino-1-ethyl-2-methyl-propyl)-phenol,
(1S,2S)-3-(3-dimethylamino-1-ethyl-2-methyl-propyl)-phenol
(+)-(1S,2S)-3-(3-dimethylamino-1-ethyl-2-methyl-propyl)-phenol
(±)-(1RS,2RS)-3-(3-dimethylamino-1-ethyl-2-methyl-propyl)-phenol
rac-(1RS,2RS)-3-(3-dimethylamino-1-ethyl-2-methyl-propyl)-phenol,
[3-(3-methoxy-phenyl)-2-methyl-pentyl]-dimethylamine,
(2R,3R)-[3-(3-methoxy-phenyl)-2-methyl-pentyl]-dimethylamine,
(−)-(2R,3R)-[3-(3-methoxy-phenyl)-2-methyl-pentyl]-dimethylamine,
(2S,3S)-[3-(3-methoxy-phenyl)-2-methyl-pentyl]-dimethylamine,
(+)-(2S,3S)-[3-(3-methoxy-phenyl)-2-methyl-pentyl]-dimethylamine,
(±)-(2RS,3RS)-[3-(3-methoxy-phenyl)-2-methyl-pentyl]-dimethylamine,
rac(2RS,3RS)-[3-(3-methoxy-phenyl)-2-methyl-pentyl]-dimethylamine,
3{[3-(p-isopropyl-phenyl-carbamoyl)-oxy-phenyl]-2-methyl-pentyl}-dimethylamine,
(2R,3R)-{3 [3-(p-isopropyl-phenyl-carbamoyl)-oxy-phenyl]-2-methyl-pentyl}-dimethylamine,
(2S,3S)-{3 [3-(p-isopropyl-phenyl-carbamoyl)-oxy-phenyl]-2-methyl-pentyl}-dimethylamine, and
(2SR,3SR)-{3 [3-(p-isopropyl-phenyl-carbamoyl)-oxy-phenyl]-2-methyl-pentyl}-dimethylamine.

19. A method according to claim 2, wherein the compound according to formula II is selected from the group consisting of:
3-(3-dimethylamino-1-ethyl-1-hydroxy-2-methyl-propyl)-phenol,
(1S,2S)-3-(3-dimethylamino-1-ethyl-1-hydroxy-2-methyl-propyl)-phenol,
(1R,2S)-3-(3-dimethylamino-1-ethyl-1-hydroxy-2-methyl-propyl)-phenol,
(1RS,2SS)-3-(3-dimethylamino-1-ethyl-1-hydroxy-2-methyl-propyl)-phenol,
(1S,2R)-3-(3-dimethylamino-1-ethyl-1-hydroxy-2-methyl-propyl)-phenol,
(1R,2R)-3-(3-dimethylamino-1-ethyl-1-hydroxy-2-methyl-propyl)-phenol,
(1RS,2RR)-3-(3-dimethylamino-1-ethyl-1-hydroxy-2-methyl-propyl)-phenol,
[3-(3-methoxy-phenyl)-2-methyl-pentan-3-ol]-dimethylamine,
(2S,3S)-[3-(3-methoxy-phenyl)-2-methyl-pentan-3-ol]-dimethylamine,
(2S,3R)-[3-(3-methoxy-phenyl)-2-methyl-pentan-3-ol]-dimethylamine,
(2SS,3RS)-[3-(3-methoxy-phenyl)-2-methyl-pentan-3-ol]-dimethylamine,
(2R,3S)-[3-(3-methoxy-phenyl)-2-methyl-pentan-3-ol]-dimethylamine,
(2R,3R)-[3-(3-methoxy-phenyl)-2-methyl-pentan-3-ol]-dimethylamine
(2RR,3RS)-[3-(3-methoxy-phenyl)-2-methyl-pentan-3-ol]-dimethylamine,
{3 [3-(p-isopropyl-phenyl-carbamoyl)-oxy-phenyl]-2-methyl-pentan-3-ol}-dimethylamine,
(2S,3R)-{3 [3-(p-isopropyl-phenyl-carbamoyl)-oxy-phenyl]-2-methyl-pentan-3-ol}-dimethylamine,
(2S,3S)-{3 [3-(p-isopropyl-phenyl-carbamoyl)-oxy-phenyl]-2-methyl-pentan-3-ol}-dimethylamine
(2SS,3RS)-{3 [3-(p-isopropyl-phenyl-carbamoyl)-oxy-phenyl]-2-methyl-pentan-3-ol}-dimethylamine,
(2R,3S)-{3 [3-(p-isopropyl-phenyl-carbamoyl)-oxy-phenyl]-2-methyl-pentan-3-ol}-dimethylamine,
(2R,3R)-{3 [3-(p-isopropyl-phenyl-carbamoyl)-oxy-phenyl]-2-methyl-pentan-3-ol}-dimethylamine and
(2RR,3RS)-{3 [3-(p-isopropyl-phenyl-carbamoyl)-oxy-phenyl]-2-methyl-pentan-3-ol}-dimethylamine.

20. A method according to claim 1, wherein the compound according to formula III is selected from the group consisting of:
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl)-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol,
(Z,E)-(2S)-3-(3-dimethylamino-1-ethenyl-2-methyl-propyl)-phenol,
3-(3-dimethylamino-1-ethenyl-2-methyl-propyl)-phenol,
(Z)-(2R)-3-(3-dimethylamino-1-ethenyl-2-methyl-propyl)-phenol,
(E)-(2R)-3-(3-dimethylamino-1-ethenyl-2-methyl-propyl-phenol,
(Z,E)-(2R)-3-(3-dimethylamino-1-ethenyl-2-methyl-propyl)-phenol,
(Z)-(2S)-3-(3-dimethylamino-1-ethenyl-2-methyl-propyl)-phenol,
(E)-(2S)-(3-dimethylamino-1-ethenyl-2-methyl-propyl)-phenol, (Z,E)-(2S)-3-(3-dimethylamino-1-ethenyl-2-methyl-propyl)-phenol,
[3-(3-methoxy-phenyl)-2-methyl-pent-3-enyl]-dimethylamine,
(Z)-(2R)-[3-(3-methoxy-phenyl)-2-methyl-pent-3-enyl]-dimethylamine,
(E)-(2R)-[3-(3-methoxy-phenyl)-2-methyl-pent-3-enyl]-dimethylamine,
(Z,E)-(2R)-[3-(3-methoxy-phenyl)-2-methyl-pent-3-enyl]-dimethylamine,
(Z)-(2S)-[3-(3-methoxy-phenyl)-2-methyl-pent-3-enyl]-dimethylamine,
(E)-(2S)-[3-(3-methoxy-phenyl)-2-methyl-pent-3-enyl]-dimethylamine,
(Z,E)-(2S)-[3-(3-methoxy-phenyl)-2-methyl-pent-3-enyl]-dimethylamine,
{3 [3-(p-isopropyl-phenyl-carbamoyl)-oxy-phenyl]-2-methyl-pent-3-enyl}-dimethylamine,
(Z)-(2R)-{3 [3-(p-isopropyl-phenyl-carbamoyl)-oxy-phenyl]-2-methyl-pent-3-enyl}-dimethylamine,
(E)-(2R)-{3 [3-(p-isopropyl-phenyl-carbamoyl)-oxy-phenyl]-2-methyl-pent-3-enyl}-dimethylamine,
(Z,E)-(2R)-{3 [3-(p-isopropyl-phenyl-carbamoyl)-oxy-phenyl]-2-methyl-pent-3-enyl}-dimethylamine,
(Z)-(2S)-{3 [3-(p-isopropyl-phenyl-carbamoyl)-oxy-phenyl]-2-methyl-pent-3-enyl}-dimethylamine,
(E)-(2S)-{3 [3-(p-isopropyl-phenyl-carbamoyl)-oxy-phenyl]-2-methyl-pent-3-enyl}-dimethylamine,
(Z,E)-(2S)-{3 [3-(p-isopropyl-phenyl-carbamoyl)-oxy-phenyl]-2-methyl-pent-3-enyl}-dimethylamine.

21. A method according to claim 2, wherein a chiral center is present in the compound according to formula II employed, at position 2 according to formula II.

22. A method according to claim 1, wherein a chiral center is present in the compound according to formula I, at position 2 according to formula I.

23. A method according to claim 1, wherein a chiral center is present in the compound according to formula III, at position 2 according to formula III.

24. A method according to claim 2, wherein the compound according to formula II is an isolated enantiomer.

25. A method according to claim 2, wherein the compound according to formula II is an isolated diastereomer.

26. A method according to claim 2, wherein the compound according to formula II is enantiomerically and diastereomerically isolated.

27. A method according to claim 2, wherein the compound according to formula II is either:
(2S),3S)-[3-(3-methoxy-phenyl)-2-methyl-pentan-3-ol]-dimethylamine,or
(2S,3R)-[3-(3-methoxy-phenyl)-2-methyl-pentan-3-ol]-dimethylamine
or
is a mixture of (2S,3S)-[3-(3-methoxy-phenyl)-2-methyl-pentan-3-ol]-dimethylamine and (2S,3R)-[3-(3-methoxy-phenyl)-2-methyl-pentan-3-ol]-dimethylamine, or (2SS, 3RS)-[3-(3-methoxy-phenyl)-2-methyl-pentan-3-ol]-dimethylamine.

28. A method according to claim 2, wherein the compound according to formula II employed is either:
(2R,3R)-[3-(3-methoxy-phenyl)-2-methyl-pentan-3-ol]-dimethylamine,or
(2R,3S)-[3-(3-methoxy-phenyl)-2-methyl-pentan-3-ol]-dimethylamine
or
is a mixture of (2R,3R)-[3-(3-methoxy-phenyl)-2-methyl-pentan-3-ol]-dimethylamine and (2R,3S)-[3-(3-methoxy-phenyl)-2-methyl-pentan-3-ol]-dimethylamine, or (2RR, 3RS)-[3-(3-methoxy-phenyl)-2-methyl-pentan-3-ol]-dimethylamine.

29. A method according to claim 2, wherein the compound according to formula II either:
(2S,3S)-1-dimethylamino-3-(3-methoxy-phenyl)-2-methyl-pentan-3-ol, or
(2S,3R)-1-dimethylamino-3-(3-methoxy-phenyl)-2-methyl-pentan-3-ol
or
is a mixture of (2S,3S)-1-dimethylamino-3-(3-methoxy-phenyl)-2-methyl -pentan-3-ol and (2S,3R)-1-dimethylamino-3-(3-methoxy-phenyl)-2-methyl -pentan-3-ol, or (2SS,3RS)-[3-(3-methoxy-phenyl)-2-methyl-pentan-3-ol]-dimethylamine.

30. A method according to claim 2, wherein the compound according to formula II is either:
(2R,3R)-1-dimethylamino-3-(3-methoxy-phenyl)-2-methyl-pentan-3-ol, or
(2R,3S)-1-dimethylamino-3-(3-methoxy-phenyl)-2-methyl-pentan-3-ol
or
is a mixture of (2R,3R)-1-dimethylamino-3-(3-methoxy-phenyl)-2-methyl -pentan-3-ol and (2R,3S)-1-dimethylamino-3-(3-methoxy-phenyl)-2-methyl -pentan-3-ol, or (2RR,3RS)-[3-(3-methoxy-phenyl)-2-methyl-pentan-3-ol]-dimethylamine.

31. A method according to claim 2, wherein organic acids or halogen halide acids are used in the initial step.

32. A method according to claim 21, wherein formic acid is used in the initial step.

33. A method according to claim 21, wherein hydrochloric acid is used in the initial step.

34. A method according to claim 21, wherein hydrobromic acid is used in the initial step.

35. A method according to claim 33, wherein the hydrochloric acid in the initial step is >20%.

36. A method according to claim 1, further comprising the step of cystallizing with hydrochloric acid the compounds according to formula III which have undergone elimination.

37. A method according to claim 2, wherein the reaction time of the initial step is between 2 and 10 h.

38. A method according to claim 2, wherein the reaction temperature in the initial step is between 35 and 100° C.

39. A method according to claim 2, wherein the solvent in the initial step is selected from:
$H_2O$ or alcohol or aqueous alcohol solutions.

40. A method according to claim 2, wherein the solvent in the initial step is an aqueous acid.

41. A method according to claim 2, wherein in the initial step, the compound according to formula II employed is dissolved in aqueous acid.

42. A method according to claim 24, wherein, in the initial step, the compound according to formula II employed is dissolved in aqueous hydrochloric acid.

43. A method according to claim 27, wherein, in the initial step, the compound according to formula II employed is dissolved in aqueous hydrochloric acid.

44. A method according to claim 1, wherein the solvent is selected from:
$H_2O$ or alcohol or aqueous alcoholic or aqueous acidic solutions.

45. A method according to claim 1, wherein the solvent is selected from:
$H_2O$ or ethanol or aqueous ethanolic solution or aqueous hydrochloric acid.

46. A method according to claim 1, wherein, the catalyst used is palladium-on-active charcoal or palladium(II) chloride.

47. A method according to claim 1, wherein, the catalyst used is palladium-on-active charcoal provided in a range of 1-10 wt. %.

48. A method according to claim 1, wherein the temperature is kept between 20 and 40° C.

49. A method according to claim 1, wherein an inert gas atmosphere is applied before the hydrogenation.

50. A method according to claim 1, wherein the hydrogenation step takes place under a hydrogen pre-pressure of 3-10 bar,
or
the hydrogenation step takes place under a hydrogen internal pressure of 0.5-3 bar.

51. A method according to claim 2, wherein the starting substances are dissolved in excess solvent at the start.

52. A method according to claim 2, wherein the solvent for both steps is an aqueous acidic solution.

53. A method according to claim 2, wherein no product is isolated between the initial step and the hydrogenation step.

54. A method according to claim 53, wherein the starting substances are dissolved in excess solvent at the start.

55. A method according to claim 2, wherein the compound according to formula II employed is dissolved in aqueous acid.

56. A method according to claim 55, wherein the compound according to formula II employed is dissolved in aqueous hydrochloric acid.

57. A method according to claim 1 wherein the products are precipitated with acid or acid gas at the end of the process.

58. A method according to claim 1, wherein the products are precipitated in an organic solvent with acid or acid gas at the end of the process.

* * * * *

(12) INTER PARTES REEXAMINATION CERTIFICATE (1047th)
United States Patent
Hell et al.

(10) Number: US 7,417,170 C1
(45) Certificate Issued: Feb. 3, 2015

(54) PROCESS FOR THE PREPARATION OF SUBSTITUTED 3-ARYL-BUTYLAMINE COMPOUNDS

(75) Inventors: Wolfgang Hell, Aachen (DE); Markus Kegel, Aachen (DE); Bernhard Akteries, Aachen (DE); Helmut Buschmann, Esplugues de Llobregat (ES); Jorg Holenz, Barcelona (ES); Harmut Loebermann, Aachen (DE); Detlef Heller, Rostock (DE); Hans-Joachim Drexler, Rostock (DE); Stefan Gladow, Buchs (CH)

(73) Assignee: Gruenenthal GmbH, Aachen (DE)

Reexamination Request:
No. 95/002,077, Aug. 16, 2012

Reexamination Certificate for:
Patent No.: 7,417,170
Issued: Aug. 26, 2008
Appl. No.: 11/294,449
Filed: Dec. 6, 2005

Related U.S. Application Data

(63) Continuation of application No. PCT/EP2004/006027, filed on Jun. 4, 2004.

(30) Foreign Application Priority Data

Jun. 6, 2003 (DE) .................. 103 26 097

(51) Int. Cl.
| | |
|---|---|
| *C07C 209/70* | (2006.01) |
| *C07C 213/08* | (2006.01) |
| *C07C 211/27* | (2006.01) |
| *C07C 211/28* | (2006.01) |
| *C07C 215/54* | (2006.01) |
| *C07C 217/62* | (2006.01) |

(52) U.S. Cl.
CPC .............. *C07C 209/70* (2013.01); *C07C 213/08* (2013.01); *C07C 211/27* (2013.01); *C07C 211/28* (2013.01); *C07C 215/54* (2013.01); *C07C 217/62* (2013.01)
USPC ............................................ 564/358; 564/375

(58) Field of Classification Search
None
See application file for complete search history.

(56) References Cited

To view the complete listing of prior art documents cited during the proceeding for Reexamination Control Number 95/002,077, please refer to the USPTO's public Patent Application Information Retrieval (PAIR) system under the Display References tab.

*Primary Examiner* — Evelyn Huang

(57) ABSTRACT

Methods for the dehydration of substituted 1-amino-3-aryl-butan-3-ol compounds for the preparation of substituted 3-aryl-butyl-amine compounds.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 2 are cancelled.

New claims 59-64 are added and determined to be patentable.

Claims 3-58 were not reexamined.

59. *A method for the preparation of a substituted 3-aryl-butyl-dimethylamine compound corresponding to formula I,*

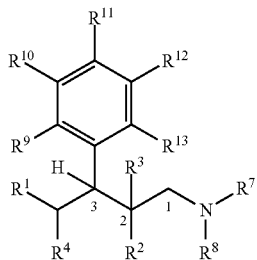

I

*wherein*
  *$R^1$ is $C_{1-3}$-alkyl, which is branched or unbranched,*
  *$R^2$ is $C_{1-4}$-alkyl, which is branched or unbranched,*
  *$R^3$ is H,*
  *$R^4$ is H,*
  *$R^7$ is $CH_3$,*
  *$R^8$ is $CH_3$,*
  *$R^9$ to $R^{13}$ in each case independently of one another are chosen from H, OH, and $OR^{14}$, where $R^{14}$ is chosen from branched or unbranched $C_{1-6}$-alkyl and benzyl in each case in the form of one of its stereoisomers, or in the form of a mixture of stereoisomers, or in each case in the form of a physiologically acceptable salt, or in each case in the form of a solvate,*
*said method comprising:*
  (a) *reacting a 1-dimethylamino-3-aryl-butan-3-ol compound corresponding to formula II with an acid,*

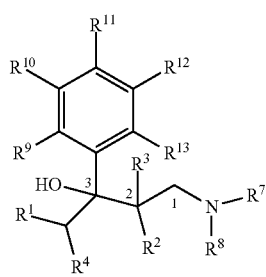

II

*to produce a substituted 3-aryl-but-3-enyl-dimethylamine compound corresponding to formula III,*

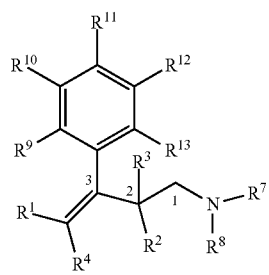

III

*wherein the stereochemistry at position 2 according to formulas II and III remains unchanged, and*
  (b) *hydrogenating the substituted 3-aryl-but-3-enyl-dimethylamine compound corresponding to formula III in the presence of a platinum or palladium catalyst and hydrogen to produce the substituted 3-aryl-butyl-dimethylamine compound corresponding to formula I,*
*further comprising the step of crystallizing with hydrochloric acid the compounds according to formula III which have undergone elimination.*

60. *A method for the preparation of a substituted 3-aryl-butyl-dimethylamine compound corresponding to formula I,*

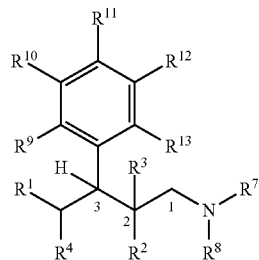

I

*wherein*
  *$R^1$ is $C_{1-3}$-alkyl, which is branched or unbranched,*
  *$R^2$ is $C_{1-4}$-alkyl, which is branched or unbranched,*
  *$R^3$ is H,*
  *$R^4$ is H,*
  *$R^7$ is $CH_3$,*
  *$R^8$ is $CH_3$,*
  *$R^9$ to $R^{13}$ in each case independently of one another are chosen from H, OH, and $OR^{14}$, where $R^{14}$ is chosen from branched or unbranched $C_{1-6}$-alkyl and benzyl in each case in the form of one of its stereoisomers, or in the form of a mixture of stereoisomers, or in each case in the form of a physiologically acceptable salt, or in each case in the form of a solvate,*
*said method comprising:*
  (a) *reacting a 1-dimethylamino-3-aryl-butan-3-ol compound corresponding to formula II with an acid,*

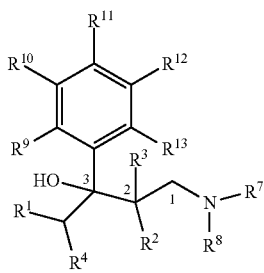

to produce a substituted 3-aryl-but-3-enyl-dimethylamine compound corresponding to formula III,

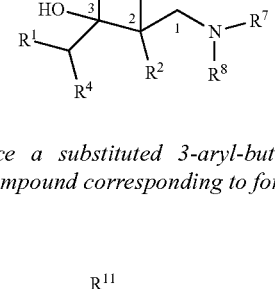

wherein the stereochemistry at position 2 according to formulas II and III remains unchanged, and (b) hydrogenating the substituted 3-aryl-but-3-enyl-dimethylamine compound corresponding to formula III in the presence of a platinum or palladium catalyst and hydrogen to produce the substituted 3-aryl-butyl-dimethylamine compound corresponding to formula I, wherein no product is isolated between step (a) and step (b).

61. A method for the preparation of a substituted 3-aryl-butyl-dimethylamine compound corresponding to formula I,

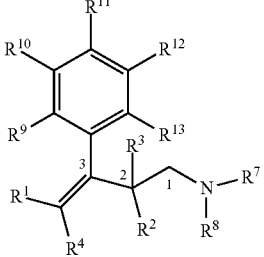

wherein
$R^1$ is $C_{1-3}$-alkyl, which is branched or unbranched,
$R^2$ is $C_{1-4}$-alkyl, which is branched or unbranched,
$R^3$ is H,
$R^4$ is H,
$R^7$ is $CH_3$,
$R^8$ is $CH_3$,
$R^9$ to $R^{13}$ in each case independently of one another are chosen from H, OH, and $OR^{14}$, where $R^{14}$ is chosen from branched or unbranched $C_{1-6}$-alkyl and benzyl in each case in the form of one of its stereoisomers, or in the form of a mixture of stereoisomers, or in each case in the form of a physiologically acceptable salt, or in each case in the form of a solvate,
said method comprising:

(a) reacting a 1-dimethylamino-3-aryl-butan-3-ol compound corresponding to formula II with an acid,

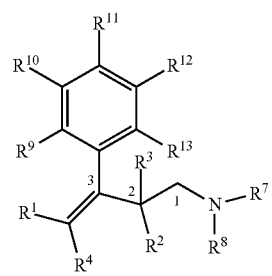

to produce a substituted 3-aryl-but-3-enyl-dimethylamine compound corresponding to formula III,

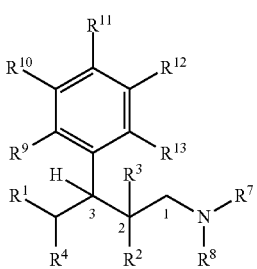

wherein the stereochemistry at position 2 according to formulas II and III remains unchanged, and (b) hydrogenating the substituted 3-aryl-but-3-enyl-dimethylamine compound corresponding to formula III in the presence of a platinum or palladium catalyst and hydrogen to produce the substituted 3-aryl-butyl-dimethylamine compound corresponding to formula I, wherein the products obtained from step (b) are precipitated with acid or acid gas at the end of the process.

62. A method for the preparation of a substituted 3-aryl-butyl-dimethylamine compound corresponding to formula I,

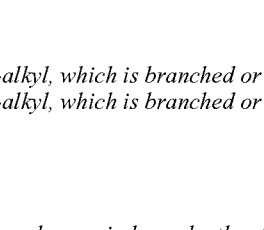

wherein
$R^1$ is $C_{1-3}$-alkyl, which is branched or unbranched,
$R^2$ is $C_{1-4}$-alkyl, which is branched or unbranched,
$R^3$ is H,
$R^4$ is H, $R^7$ is $CH_3$,
$R^8$ is $CH_3$,
$R^9$ to $R^{13}$ in each case independently of one another are chosen from H, OH, and $OR^{14}$, where $R^{14}$ is chosen from branched or unbranched $C_{1-6}$-alkyl and benzyl in each case in the form of one of its stereoisomers, or in the form of a mixture of stereoisomers, or in each case in the form of a physiologically acceptable salt, or in each case in the form of a solvate, said method comprising:

(a) reacting a 1-dimethylamino-3-aryl-butan-3-ol compound corresponding to formula II with an acid,

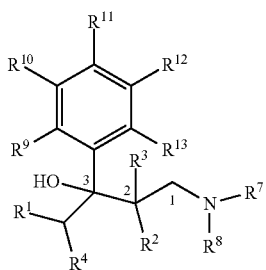

II to produce a substituted 3-aryl-but-3-enyl-dimethylamine compound corresponding to formula III,

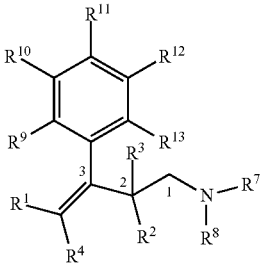

III wherein the stereochemistry at position 2 according to formulas II and III remains unchanged, and (b) hydrogenating the substituted 3-aryl-but-3-enyl-dimethylamine compound corresponding to formula III in the presence of a platinum or palladium catalyst and hydrogen to produce the substituted 3-aryl-butyl-dimethylamine compound corresponding to formula I, wherein the products obtained from step (b) are precipitated in an organic solvent with acid or acid gas at the end of the process.

63. A method for the preparation of a substituted 3-aryl-butyl-dimethylamine compound corresponding to formula I,

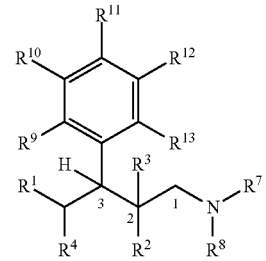

I wherein $R^1$ is $C_{1-3}$-alkyl, which is branched or unbranched,
$R^2$ is $C_{1-4}$-alkyl, which is branched or unbranched,
$R^3$ is H,
$R^4$ is H,
$R^7$ is $CH_3$,
$R^8$ is $CH_3$, $R^9$ to $R^{13}$ in each case independently of one another are chosen from H, OH, and $OR^{14}$, where $R^{14}$ is chosen from branched or unbranched $C_{1-6}$-alkyl and benzyl in each case in the form of one of its stereoisomers, or in the form of a mixture of stereoisomers, or in each case in the form of a physiologically acceptable salt, or in each case in the form of a solvate, said method comprising:

(a) reacting a 1-dimethylamino-3-aryl-butan-3-ol compound corresponding to formula II with an acid,

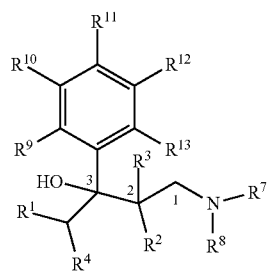

II to produce a substituted 3-aryl-but-3-enyl-dimethylamine compound corresponding to formula III,

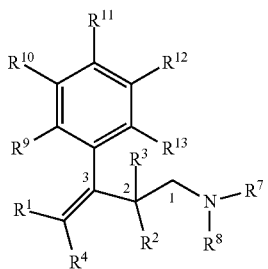

III wherein the stereochemistry at position 2 according to formulas II and III remains unchanged, and (b) hydrogenating the substituted 3-aryl-but-3-enyl-dimethylamine compound corresponding to formula III in the presence of a platinum or palladium catalyst and hydrogen to produce the substituted 3-aryl-butyl-dimethylamine compound corresponding to formula I, wherein the compounds according to formula I are in the configuration Ia

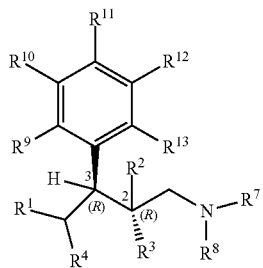

Ia and optionally may be in the form of a physiologically acceptable salt or in the form of a solvate,
wherein the method yields configuration Ia in excess of 70%.

64. A method for the preparation of a substituted 3-aryl-butyl-dimethylamine compound corresponding to formula I,

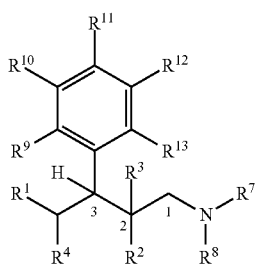

I wherein
- $R^1$ is $C_{1-3}$-alkyl, which is branched or unbranched,
- $R^2$ is $C_{1-4}$-alkyl, which is branched or unbranched,
- $R^3$ is H,
- $R^4$ is H,
- $R^7$ is $CH_3$,
- $R^8$ is $CH_3$,
- $R^9$ to $R^{13}$ in each case independently of one another are chosen from H, OH, and $OR^{14}$, where $R^{14}$ is chosen from branched or unbranched $C_{1-6}$-alkyl and benzyl in each case in the form of one of its stereoisomers, or in the form of a mixture of stereoisomers, or in each case in the form of a physiologically acceptable salt, or in each case in the form of a solvate, said method comprising:
(a) reacting a 1-dimethylamino-3-aryl-butan-3-ol compound corresponding to formula II with an acid,

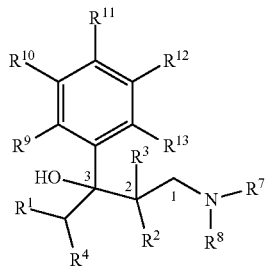

II to produce a substituted 3-aryl-but-3-enyl-dimethylamine compound corresponding to formula III,

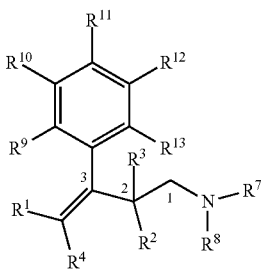

III wherein the stereochemistry at position 2 according to formulas II and III remains unchanged, and
(b) hydrogenating the substituted 3-aryl-but-3-enyl-dimethylamine compound corresponding to formula III in the presence of a platinum or palladium catalyst and hydrogen to produce the substituted 3-aryl-butyl-dimethylamine compound corresponding to formula I,
wherein the reaction of step (b) is carried in a solvent,
wherein the solvent in step (b) is an aqueous hydrochloric acid solution.

* * * * *